(12) United States Patent
Barlow et al.

(10) Patent No.: US 8,715,281 B2
(45) Date of Patent: May 6, 2014

(54) TREATMENT DEVICE FOR ENDOSCOPE

(75) Inventors: David E. Barlow, Coopersburg, PA (US); Kunihide Kaji, Tokyo (JP); Takayuki Suzuki, Yokohama (JP); Masatoshi Sato, Yokohama (JP); Kensuke Hayashi, Yokohama (JP); Takayasu Mikkaichi, Tokyo (JP); Junji Shiono, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 1550 days.

(21) Appl. No.: 11/715,166

(22) Filed: Mar. 7, 2007

(65) Prior Publication Data

US 2008/0015409 A1  Jan. 17, 2008

Related U.S. Application Data

(60) Provisional application No. 60/781,350, filed on Mar. 9, 2006.

(51) Int. Cl.
  *A61B 18/00* (2006.01)
  *A61B 1/018* (2006.01)
  *A61B 17/94* (2006.01)

(52) U.S. Cl.
  USPC ............... 606/46; 606/47; 606/113; 600/104; 600/106

(58) Field of Classification Search
  USPC .................. 606/46, 47, 113; 600/104, 106
  See application file for complete search history.

(56) References Cited

U.S. PATENT DOCUMENTS

| | | | | |
|---|---|---|---|---|
| 4,493,320 A | * | 1/1985 | Treat | 606/47 |
| 4,718,419 A | * | 1/1988 | Okada | 606/47 |
| 5,108,406 A | * | 4/1992 | Lee | 606/106 |
| 5,158,561 A | * | 10/1992 | Rydell et al. | 606/113 |
| 5,163,973 A | * | 11/1992 | Ellis | 23/301 |
| 5,254,117 A | * | 10/1993 | Rigby et al. | 606/46 |
| 5,318,564 A | * | 6/1994 | Eggers | 606/47 |
| 5,376,094 A | * | 12/1994 | Kline | 606/113 |
| 5,535,759 A | | 7/1996 | Wilk | |
| 5,536,248 A | * | 7/1996 | Weaver et al. | 604/506 |

(Continued)

FOREIGN PATENT DOCUMENTS

| | | |
|---|---|---|
| JP | S62-64355 | 3/1987 |
| JP | H7-265420 | 10/1995 |

(Continued)

OTHER PUBLICATIONS

Chinese Official Action dated Oct. 29, 2010 together with an English language translation.

(Continued)

*Primary Examiner* — Linda Dvorak
*Assistant Examiner* — Kaitlyn Smith
(74) *Attorney, Agent, or Firm* — Scully, Scott, Murphy & Presser, P.C.

(57) ABSTRACT

This treatment device for endoscope is used for cutting body tissue while the treatment device is retractably projected from a catheter. The treatment device includes: a control wire inserted into the catheter; and a cutting electrode mounted at the distal end of the control wire with the cutting electrode being imparted a bent configuration in advance. The cutting electrode elastically deforms in a state where the cutting electrode is retracted into the catheter, thereby assuming such a shape as to resemble the configuration of the catheter.

14 Claims, 17 Drawing Sheets

(56) References Cited

U.S. PATENT DOCUMENTS

| | | | |
|---|---|---|---|
| 6,050,995 A * | 4/2000 | Durgin | 606/47 |
| 6,071,274 A * | 6/2000 | Thompson et al. | 604/528 |
| 6,176,858 B1 * | 1/2001 | Dequesne et al. | 606/47 |
| 6,190,384 B1 | 2/2001 | Ouchi | |
| 6,231,578 B1 * | 5/2001 | Rajhansa | 606/113 |
| 6,328,734 B1 * | 12/2001 | Zappala | 606/32 |
| 6,383,183 B1 * | 5/2002 | Sekino et al. | 606/34 |
| 6,733,496 B2 * | 5/2004 | Sharkey et al. | 606/41 |
| 6,746,395 B2 * | 6/2004 | Brommersma et al. | 600/105 |
| 6,852,111 B1 * | 2/2005 | Lieber | 606/47 |
| 6,878,149 B2 * | 4/2005 | Gatto | 606/46 |
| 7,101,378 B2 * | 9/2006 | Salameh et al. | 606/113 |
| 7,147,635 B2 * | 12/2006 | Ciarrocca | 606/48 |
| 7,468,042 B2 * | 12/2008 | Turovskiy et al. | 600/564 |
| 7,722,626 B2 * | 5/2010 | Middleman et al. | 606/113 |
| 2001/0049509 A1 * | 12/2001 | Sekine et al. | 604/264 |
| 2002/0188290 A1 * | 12/2002 | Sharkey et al. | 606/41 |
| 2003/0135222 A1 * | 7/2003 | Baska | 606/113 |
| 2003/0144661 A1 * | 7/2003 | Brommersma et al. | 606/46 |
| 2003/0233099 A1 * | 12/2003 | Danaek et al. | 606/96 |
| 2004/0044343 A1 * | 3/2004 | Brommersma et al. | 606/46 |
| 2004/0092953 A1 * | 5/2004 | Salameh et al. | 606/113 |
| 2005/0043743 A1 * | 2/2005 | Dennis | 606/113 |
| 2005/0131424 A1 * | 6/2005 | Ouchi | 606/113 |
| 2005/0209609 A1 * | 9/2005 | Wallace | 606/113 |
| 2006/0095025 A1 | 5/2006 | Levine et al. | |
| 2006/0276784 A1 * | 12/2006 | Miyajima et al. | 606/46 |
| 2007/0088369 A1 * | 4/2007 | Shaw et al. | 606/113 |
| 2008/0009856 A1 * | 1/2008 | Suzuki | 606/46 |
| 2008/0009857 A1 * | 1/2008 | Yanuma | 606/46 |
| 2008/0294175 A1 * | 11/2008 | Bardsley et al. | 606/113 |
| 2009/0005778 A1 * | 1/2009 | Ducharme | 606/46 |
| 2010/0042107 A1 * | 2/2010 | Merrifield | 606/106 |
| 2010/0204710 A1 * | 8/2010 | Shaw et al. | 606/113 |

FOREIGN PATENT DOCUMENTS

| | | |
|---|---|---|
| JP | H11-318926 | 11/1999 |
| JP | 2000-201938 | 7/2000 |
| JP | 2002-330920 A | 11/2002 |
| JP | 2003-527923 | 9/2003 |
| JP | 2004-275641 | 10/2004 |
| JP | 2005-534426 | 11/2005 |
| JP | 2006-095146 A | 4/2006 |
| JP | 2006-334398 A | 12/2006 |
| WO | WO 00/12010 | 3/2000 |
| WO | WO 01/72234 A1 | 10/2001 |
| WO | WO 2004/012583 A2 | 2/2004 |
| WO | WO 2005/079901 A1 | 9/2005 |

OTHER PUBLICATIONS

Japanese Office Action dated Mar. 27, 2012 from corresponding Japanese Patent Application No. JP 2008-503912.

Japanese Office Action dated Oct. 2, 2012 from corresponding Japanese Patent Application No. JP 2008-503912.

* cited by examiner

TREATMENT DEVICE FOR ENDOSCOPE

The present invention claims the right of priority on U.S. patent application Ser. No. 60/781,350 filed on Mar. 9, 2006, with the content of which is incorporated herein by reference.

BACKGROUND OF THE INVENTION

1. Field of the Invention

The present invention relates to a treatment device for an endoscope for coagulating and cutting body tissue in the body by using an endoscope.

2. Description of Related Art

In the field of endoscopic surgery there are a variety of prior art devices for cutting body tissue. These devices include various needle-tipped cutting electrodes, crescent and oval shaped snares, papillotomy/sphincterotomy devices, fixed hook-shaped electrodes, insulator chipped wire electrodes, and other designs that are intended for specific therapeutic applications. While there are some devices which are too large to pass through the endoscope's channel and must be attached to the exterior surface of the endoscope, or back-loaded into the channel of the endoscope, most of these devices collapse into the sheath of the treatment device, and thereby transform into a size and shape that can pass freely through the channel of the endoscope. Likewise, the present invention focuses on an apparatus that can collapse and pass through the channel of the endoscope.

A basic tenet of surgery is that cutting body tissue, whether by a sharp scalpel (i.e., a cold cut) or by electrosurgical current (i.e., hot cut), is best performed when traction is applied to the body tissue. Traction puts tension on the flaccid body tissue being cut and facilitates separation of the parts being incised. In open surgery, traction is applied by pulling or stretching the body tissue with the surgeon's fingers or by holding it with a treatment device(s). In open surgery, the surgeon has full and easy control over the movement of the scalpel or electrosurgical cutting tool.

SUMMARY OF THE INVENTION

A treatment device for endoscope of the present invention is used for cutting body tissue while the treatment device is retractably projected from a catheter. The treatment device includes: a control wire inserted into the catheter; and a cutting electrode mounted at the distal end of the control wire with the cutting electrode being imparted a bent configuration in advance. The cutting electrode elastically deforms in a state where the cutting electrode is retracted into the catheter, thereby assuming the shape of the catheter.

The treatment device for endoscope of the present invention may further include a restraint instrument for restraining the leading end of the cutting electrode projected from the catheter.

In the treatment device for endoscope of the present invention, the restraint instrument may be a grasping forceps for grasping the leading end of the cutting electrode. The use of the grasping forceps makes it possible to easily restrain the leading end of the cutting electrode. Incidentally, the restraint instrument may be inserted into a channel provided at a portion into which the endoscope is inserted or the restraint instrument may be inserted into the catheter together with the treatment device for endoscope of the present invention.

In the treatment device for endoscope of the present invention, a loop may be provided at the leading end of the restraint instrument, and a hook portion of hooking the loop may be provided at the leading end of the cutting electrode. Alternatively, the loop may be provided at the leading end of the cutting electrode, and the hook portion of hooking the loop may be provided at the leading end of the restraint instrument.

In the treatment device for endoscope of the present invention, the restraint instrument may be projected from an opening at the distal end of the catheter, and the cutting electrode may be projected from a through hole formed on the side wall at the distal end of the catheter. Alternatively, the cutting electrode may be projected from the opening at the distal end of the catheter, and the restraint instrument may be provided on the side wall at the distal end of the catheter.

In the treatment device for endoscope of the present invention, the cutting electrode may have a three-dimensional bent configuration. Further, the treatment device for endoscope of the present invention may be additionally provided with a flexible sheath to be inserted into the catheter, together with the control wire, with the control wire being inserted thereinside, and a bent configuration is imparted in advance to the distal end of flexible sheath.

The treatment device for endoscope of the present invention may further include a cap wrapped at the distal end of the catheter and having a contact face of holding the body tissue to be cut between itself and the cutting electrode. Further, the cap may be provided with a cutting-electrode fixing portion for fixing the leading end of the cutting electrode.

In the treatment device for endoscope of the present invention, the cutting electrode may be bent approximately in a V-letter shape, and the cutting electrode may have a proximal portion continuing to the control wire and a distal portion continuing to the proximal portion, the distal portion being folded back with respect to the proximal portion. A space between the proximal portion and the distal portion may be made narrower as it moves away from the distal end of the control wire.

In the treatment device for endoscope of the present invention, the cutting electrode may have a cross section in which the length of the arc of the cutting electrode in the first axis direction from the inside to the outside is longer than the length in the second axis direction orthogonal to the first axis.

In the treatment device for endoscope of the present invention, the cutting electrode may be covered with an insulator at a portion excluding a portion which is pressed to the body tissue to be cut.

The treatment device for endoscope of the present invention may further include a projected-length adjusting portion for adjusting a projected length from the distal end of the catheter in the cutting electrode. Further, the projected-length adjusting portion may be provided with a stopper for regulating a maximum projected length of the cutting electrode.

In the treatment device for endoscope of the present invention, the catheter may be made of an isolating material, and a metal sheath may be fitted inside the distal end of the catheter.

In the treatment device for endoscope of the present invention, an insulator may be provided at the leading end of the cutting electrode.

The treatment device for endoscope of the present invention is used for cutting body tissue in the body. The treatment device includes: a catheter; a control wire inserted into the catheter, and a cutting electrode mounted at the distal end of the control wire with the cutting electrode being imparted a bent configuration in advance. The catheter is provided with a lumen for inserting the control wire and another lumen for inserting a restraint instrument for restraining the leading end of the cutting electrode projected from the catheter.

DESCRIPTION OF THE PREFERRED EMBODIMENTS

Figure 1:
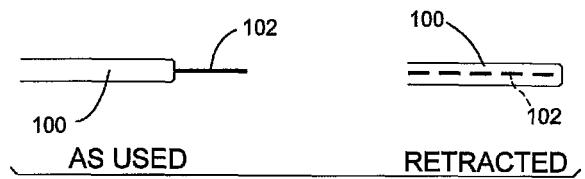
FIG. 1 is a view illustrating a cutting electrode mounted on a known treatment device for endoscope, showing a state in which the cutting electrode is used for treatment and that in which it is retracted into a catheter.

Many applications of endoscopic surgery require the cutting or incision of body tissue using radio frequency (RF) electrosurgical current. A variety of prior art devices are available for RF treatment. Some of these devices are specifically linked to the type of endoscope being used; for example, the cutting loops designed specifically for transurethral resection with a urological resecto scope. Others are designed to perform a specific type of procedure through generic endoscopes; for example, papillotomy knife (sphincterotomy knife) designed specifically to incise the Papilla of Vater, and snares designed specifically to remove colon polyps—all performed through standard flexible endoscopes. Other cutting devices are designed for more generic applications; such as needle-tipped electrodes which can be used for a variety of endoscopic cutting applications.

The ability to apply traction to body tissue is a key element in cutting body tissue easily and precisely. In open surgery the body tissue being excised is usually grasped with a treatment device and stretched to place it under slight tension in order to stabilize the body tissue, to guide the incision, and to separate the incised parts. In a typical situation the body tissue is held with a grasping instrument(s), while a scalpel or electrosurgical cutting device is used to incise the body tissue.

In laparoscopic surgery, this same technique is often used. The body tissue is grasped and held with forceps inserted through one laparoscopic port, while it is incised by means of a cutting electrode placed through a separate laparoscopic port.

In applications of flexible endoscopy, the ability to put traction on the body tissue being cut is often difficult or impossible with devices currently available. Some devices, such as papillotomy knife, are designed so that the device itself puts pressure on the body tissue as the cut is being made. In the case of a papillotomy knife, the operator closes the handle on the device to bow the tip of the papillotomy knife, forcing the cutting wire into the stretched sphincter muscle. The degree of tension placed on the body tissue by the cutting electrode is controlled by the degree to which the operator closes the handle of the papillotomy knife.

However, in many applications of flexible endoscopy, the cutting electrode (e.g., cutting wire) is pressed into the body tissue by means of moving the leading end of the endoscope itself. Movement of the leading end of the endoscope is accomplished by movements of the shaft of the endoscope, and/or manipulation of the angle control knobs of the endoscope. Both of these maneuvers are often awkward and imprecise compared to using handheld cutting tools. Furthermore, in endoscopic surgery, the movement of the cutting tool is often achieved by moving the endoscope itself—an often difficult and cumbersome procedure.

The easiest maneuver to make with an electrode which passes through the channel of a flexible endoscope is to pull back on the shaft of the device, thereby withdrawing it into the channel of the endoscope. Movement of the electrode towards the endoscope leading end by withdrawing the electrode shaft into the endoscope's channel has several advantages over moving the endoscope itself: 1) the electrode moves in a predefined, easily predicted direction—directly towards the leading end of the endoscope, 2) the electrode can place considerable force on the body tissue, usually greater force than can be asserted by moving the leading end of the endoscope itself, and 3) if the electrode is placed behind the body tissue being cut, withdrawal of the electrode will put traction on the body tissue being cut, while at the same time maintaining a clear view of the site of the incision.

Figure 2:
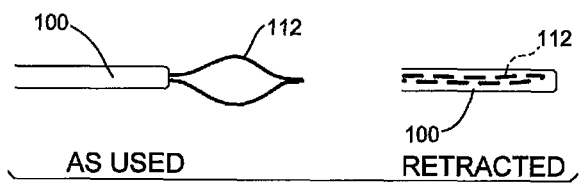
FIG. 2 is a view illustrating a cutting electrode mounted on a known treatment device for endoscope, showing a state in which the cutting electrode is used for treatment and that in which it is retracted into a catheter.
Figure 3:
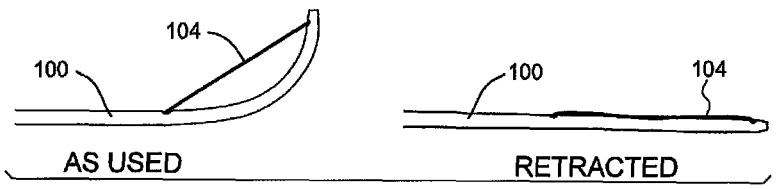
FIG. 3 is a view illustrating a cutting electrode mounted on a known treatment device for endoscope, showing a state in which the cutting electrode is used for treatment and that in which it is retracted into a catheter.
Figure 4:
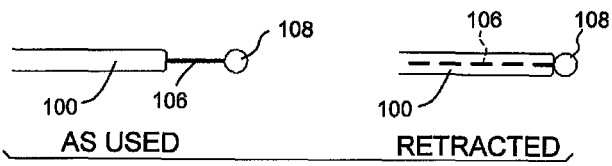
FIG. 4 is a view illustrating a cutting electrode mounted on a known treatment device for endoscope, showing a state in which the cutting electrode is used for treatment and that in which it is retracted into a catheter.
Figure 5:
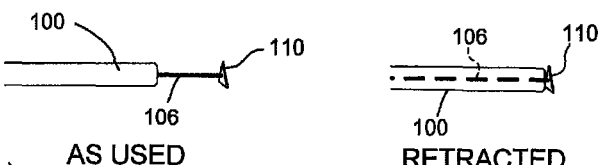
FIG. 5 is a view illustrating a cutting electrode mounted on a known treatment device for endoscope, showing a state in which the cutting electrode is used for treatment and that in which it is retracted into a catheter.
Figure 6:
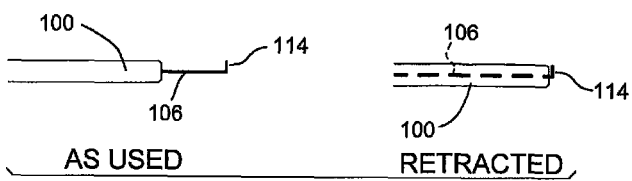
FIG. 6 is a view illustrating a cutting electrode mounted on a known treatment device for endoscope, showing a state in which the cutting electrode is used for treatment and that in which it is retracted into a catheter.

FIG. 1 through to FIG. 6 schematically illustrate the distal end of several prior art wire-type cutting electrodes which are in common use for endoscopic surgery. FIG. 1 illustrates a needle electrode having a projected cutting wire 102 and FIG. 2 illustrates a snare having a loop cutting wire 112. FIG. 3 illustrates papillotomy knive having a cutting wire 104. The papillotomy knive shown in FIG. 3 bends the distal end of the catheter 100 upon application of tensile force and closely attach to the catheter 100 upon release of the tensile force. FIG. 4 through FIG. 6 illustrate an electrode having a cutting wire 106. The distal end 108 of the cutting wire 106 shown in FIG. 4 is insulated. A triangular-shaped metal chip 110 is provided at the leading end of the cutting wire 106 shown in FIG. 5. A small fixed-type hook-shaped wire chip 114 is provided at the leading end of the cutting wire 106 shown in FIG. 6. In individual devices, the electrode wire can be closely attached to the catheter 100 or retracted into the catheter 10 so as to be passed through the endoscope's channel. FIG. 1 through FIG. 6 illustrate a state in which the distal end of the electrode wire is exposed from the catheter 100 and a state in which the distal end of the electrode wire is retracted into the catheter 100 so as to be passed through the endoscope's channel.

Some of these devices are designed for a specific application. For example, snares in FIG. 2 are designed to be looped over a protruding piece of body tissue, most typically a polyp, and the body tissue is cut off by closing the snare's handle, thereby pulling the cutting wire through the body tissue as RF current is applied. papillotomy knive in FIG. 3 are specifically designed to be inserted into a papillary orifice such as the ductal opening of the Papilla of Vater. The handle of the papillotomy knife is then "closed" to put tension on the cutting wire 104 and to bow the leading end of the catheter 100. This presses the cutting wire 104 against the body tissue as RF current is applied and the incision is made.

In the other devices illustrated in FIG. 1 and FIG. 4 through FIG. 6, manipulation of the handle of the device during the therapeutic procedure is not necessary. The handle is used only to place the electrode in its exposed, ready for use, position. The endoscope itself must then be manipulated to press the cutting electrode against the body tissue and to control the direction of movement of the electrode through the body tissue. As mentioned above, manipulating the cutting electrode by manipulating the endoscope is often awkward and provides poor control over the direction of the electrode, or the cutting direction.

Figure 7:
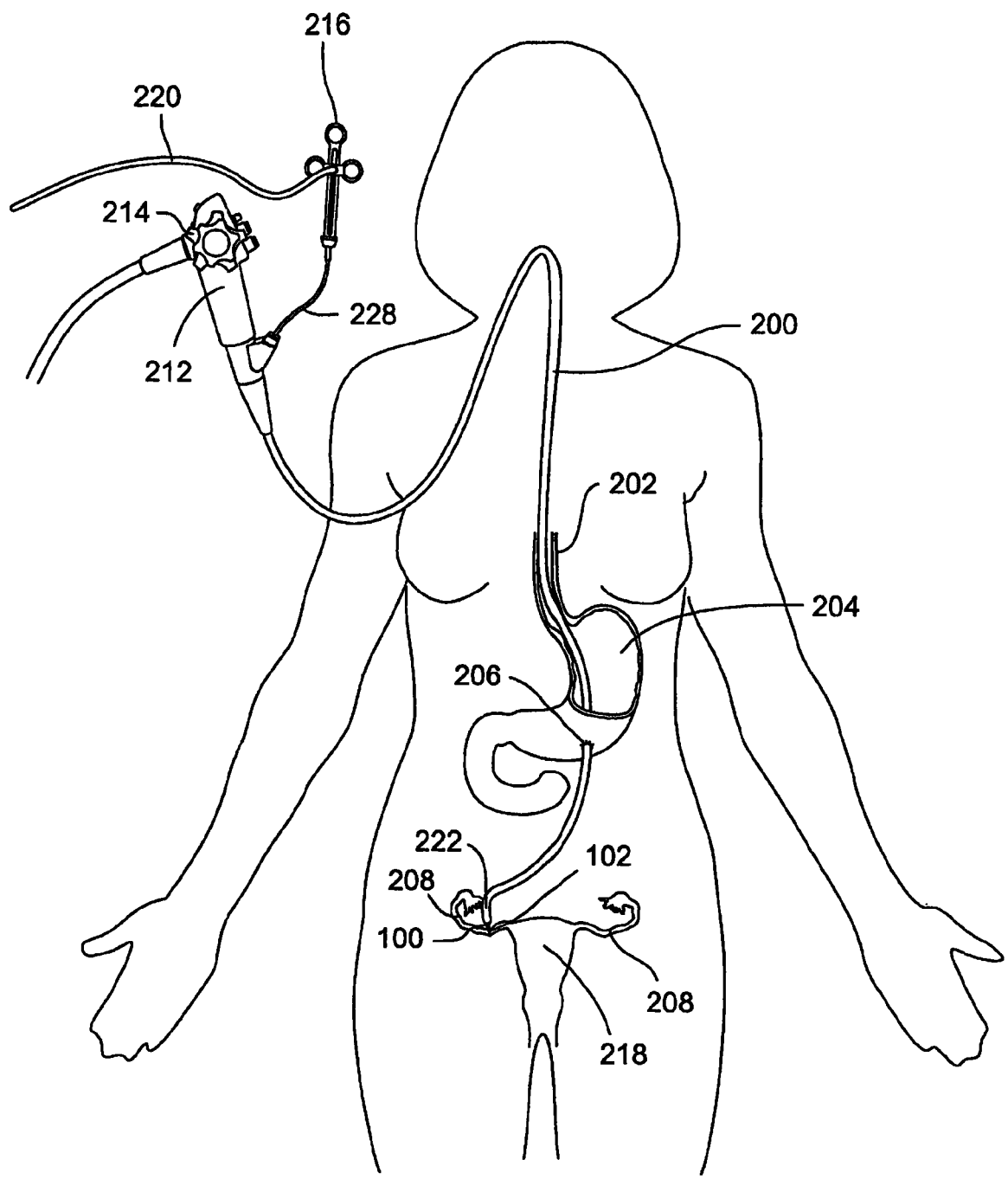
FIG. 7 is a schematic sectional view of the body of a female patient from a frontal view, showing a state that a known treatment device for endoscope is passed into a channel of an insertion tube of the endoscope and the cutting electrode of the treatment device is disposed at an appropriate position for incising the right fallopian tube in a female patient.

FIG. 7 schematically illustrates the use of a flexible endoscope to incise the fallopian tube of a female patient with a needle electrode. In this particular instance the insertion tube 200 of the flexible endoscope 212 has been inserted into the patient's mouth (not illustrated), through the patient's esophagus into the patient's stomach 204. An incision 206 in the wall of the stomach allows the endoscope insertion tube 200 to pass from the interior of the stomach into the peritoneal cavity and to approach the pelvic organs of the patient. For simplicity only the patient's uterus 218 and fallopian tubes 208 are shown. A cutting wire 102 is protruded from the distal end of a catheter 100 passed through the endoscope's channel (inner lumen) and is pressed against the fallopian tube in order to incise it. A handle 216 attached to the proximal end of the catheter 100 allows the operator to retract and extend the cutting wire 102 into and out of the proximal end of the catheter 100. The handle 216 is also connected to an active cord 220 which supplies RF current from an RF generator (not illustrated) to the electrode wire.

While the handle 216 is used to protrude and retract the cutting wire 102 from the distal end of the catheter 100, it has no role in positioning the cutting wire 102 along the body tissue and moving the cutting wire 102 in the intended cutting direction. The operator accomplishes these tasks by manipulating the insertion tube 200 of the endoscope and by operating the angle control knobs 214 which control the movement of the distal end of the endoscope.

Figure 8:
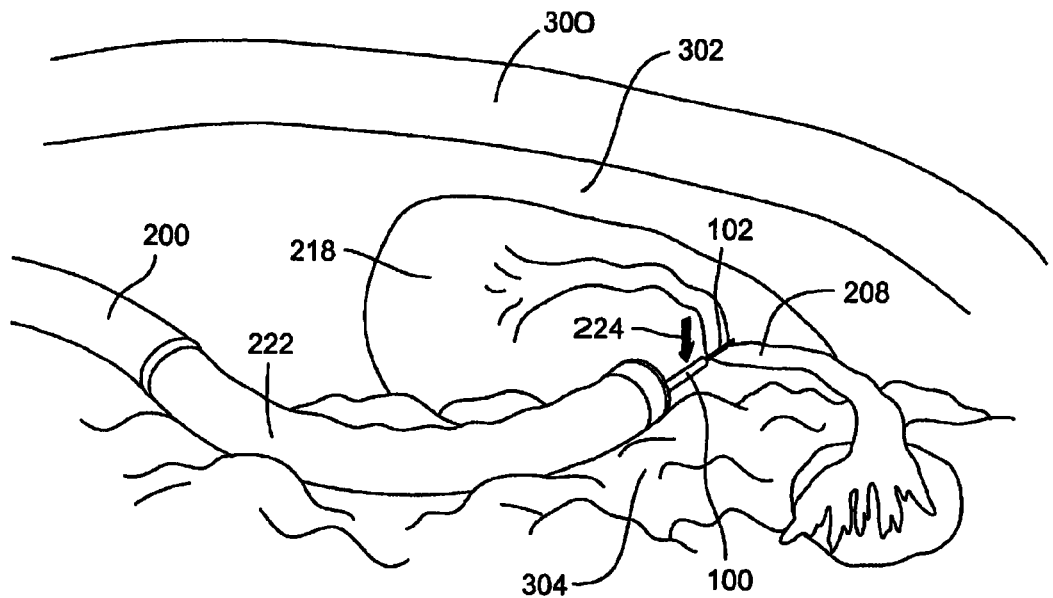
FIG. 8 is a schematic sectional view illustrating the right fallopian tube and adjacent body tissues in a female patient, showing a state in which a cutting electrode mounted on a known treatment device for endoscope is pressed to the fallopian tube.

FIG. 8 illustrates an enlarged view of the treatment applied to the fallopian tube. In this instance the operator is intending to cut through the fallopian tube to severe it, one step of many in a procedure to render the patient infertile. FIG. 8 illustrates the distal end of the endoscope's insertion tube 200 and a bending section 222 lying in the intraperitoneal cavity 302 of the lower abdomen of the patient. The cutting wire 102 and the catheter 100 protrude from the distal end of the insertion tube and are positioned near the patient's right fallopian tube 208. To use a needle electrode of this type in this application, the cutting wire must be pressed against the flaccid body tissue of the fallopian tube 208 as the RF current is applied to the cutting wire 102. However, in this configuration, the only means of controlling the direction in which the cutting wire 102 moves is through manipulation of the endoscope's insertion tube 200 by grasping that portion which exits from the patient's mouth, or by manipulating the angle control knobs on the endoscope. Operating the angle control knobs will change the deflection of the bending section 222 of the endoscope by remote control. Both of these maneuvers are awkward and imprecise. Furthermore, as illustrated in FIG. 8, in many situations, pressing the cutting wire 102 against the body tissue in the direction 224 shown in FIG. 8, will force the fallopian tube 208 against the underlying pelvic organs and the cutting wire 102 will likely cut and damage this body tissue as well.

Figure 9:
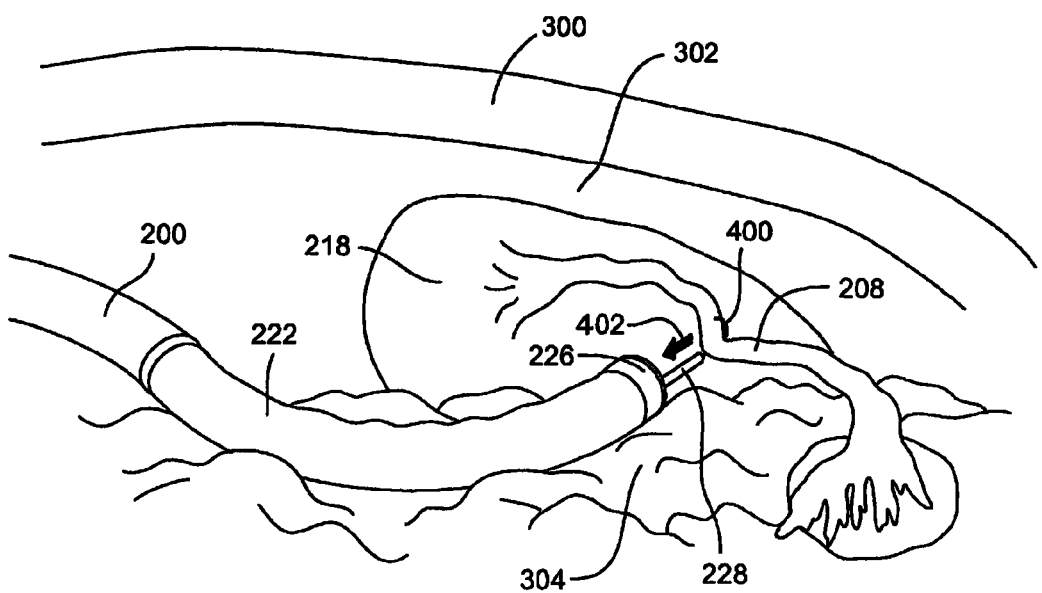
FIG. 9 is a schematic sectional view illustrating the right fallopian tube and adjacent body tissues in a female patient, showing a state in which a cutting electrode mounted on the treatment device for endoscope of the present invention is hooked onto the fallopian tube.

FIG. 9 illustrates an embodiment of the endoscope-use device of the present invention. As shown in FIG. 9, the needle electrode is replaced by the preformed spring electrode 400. The electrode 400 which protrudes from the distal end of the catheter 228 is hooked and has been placed around the distal side of the fallopian tube 208. The device elevates the fallopian tube 208 off of the pelvic organs 304 rather than pressing it into these organs. After appropriately manipulating the device so as to be around the distal end of the fallopian tube 208 and confirming that only the body tissue that is intended to be cut is contacting the preformed spring electrode 400, RF current is applied to the electrode 400 from an electrosurgical current generator connected to the proximal handle of the device (not shown). During the application of RF current, the operator pulls the catheter 228 so as to remove the electrode 400 in the direction 402 shown in FIG. 9. This action puts traction on the body tissue facilitating the cut. This action is also easily performed by simply pulling the proximal portion of the catheter which extends from the control section of the endoscope. No specific manipulations of the endoscope insertion tube 200 or bending section 222 are required.

Figure 10:
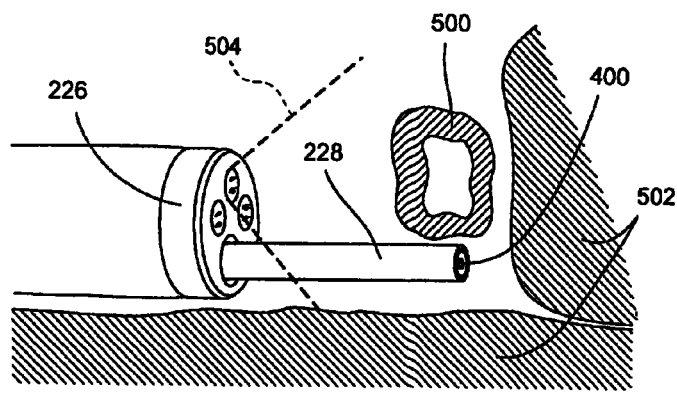
FIG. 10 is a schematic sectional view illustrating the body tissue to be cut and adjacent body tissues thereof, showing a state in which the insertion tube of the endoscope is disposed in front of the body tissue to be cut.
Figure 11:
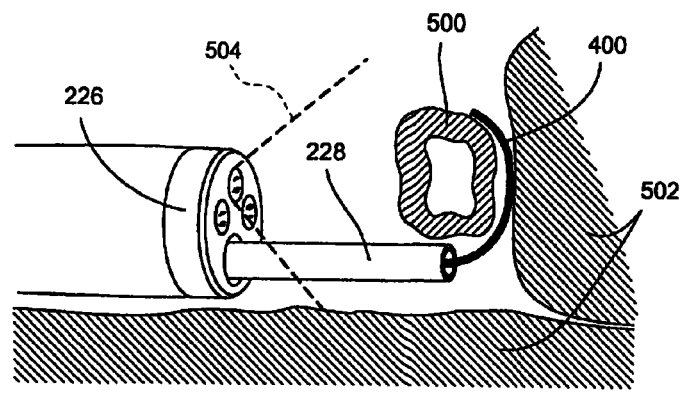
FIG. 11 is a schematic sectional view illustrating the body tissue to be cut and the adjacent body tissues thereof, showing a state in which a catheter is projected from a channel of an insertion tube of an endoscope, and a hooked cutting electrode is projected from the catheter and hooked onto the body tissue to be cut.
Figure 12:
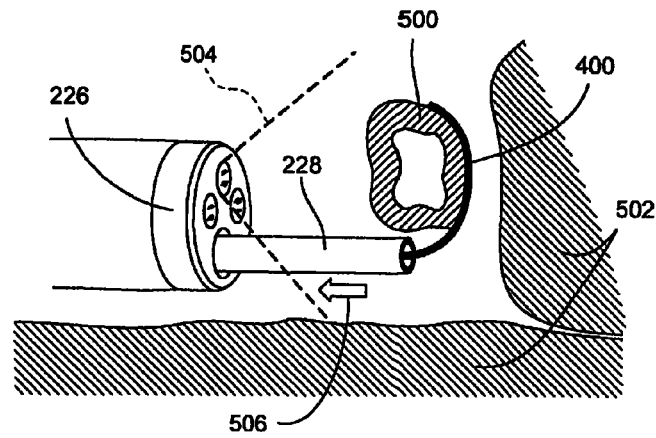
FIG. 12 is a schematic sectional view illustrating the body tissue to be cut in the body and the adjacent body tissues, showing a state in which the cutting electrode hooked onto the body tissue to be cut is pulled and a traction force is applied to the body tissue.

FIG. 10 through FIG. 12 illustrate how the device of the present invention can be used to isolate the body tissue intended to be cut from other surrounding body tissues. First, as shown in FIG. 10, the distal end 226 of the endoscope insertion tube 200 is first positioned so that the catheter 228 is placed between the body tissue 500 to be cut and other adjacent body tissues 502 that must be preserved. As shown in FIG. 11, the preformed spring electrode 400 is then protruded from the distal end of the flexible catheter 228 by manipulating the handle of the device (not shown) to allow the electrode 400 to hook the body tissue 500 to be cut. The device of the present invention, is manufactured from specific materials and by a manufacturing method used for assembling electrode elements, forms a specific hooked shape when the electrode protrudes from the distal end of the flexible catheter 228. The endoscope is then manipulated to move the body tissue to be cut away from the other adjacent body tissues 502 in order not to accidentally burn or cut them through contact with the electrified electrode 400. The operator then withdraws the flexible catheter 228 into the channel of the endoscope, pulls the body tissue 500 to be cut to separate it from all adjacent body tissues structures. The body tissue can be incised by applying RF electrosurgical current while pulling the flexible catheter 228 and moving the electrode 400 together with the distal end of the endoscope in the direction 506. The entire procedure is performed under visual control by keeping all manipulations in the field of view 504 of the endoscope.

Figure 13:
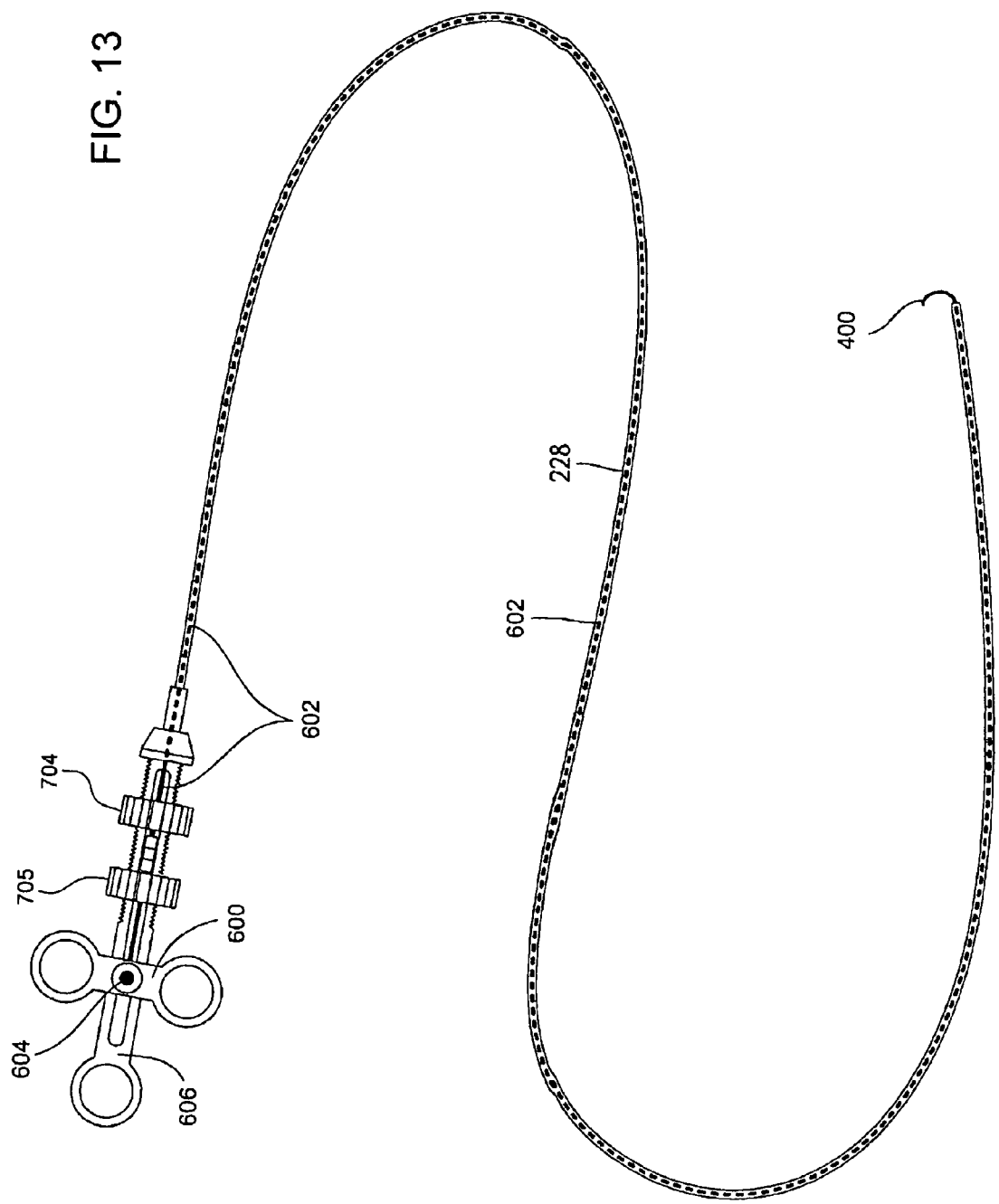
FIG. 13 is a plan view illustrating the whole constitution of the treatment device for endoscope of an embodiment of the present invention.

FIG. 13 illustrates an overall view of an treatment device for endoscope of the present invention. As shown in FIG. 13, the preformed spring electrode 400 protrudes from the distal end of a flexible catheter 228. The flexible catheter is long enough to pass completely through the channel (inner lumen) of a flexible endoscope, and has some additional length to make it convenient to use. The proximal end of the catheter 228 is connected to a handle 606. A slider 600 on the handle 606 is connected to the proximal end of a control wire 602. The control wire 602 runs through the internal lumen of the flexible catheter 228 and is attached at its distal end with the preformed spring electrode 400. As the operator moves the slider 600 of the handle back and forth, this action moves the control wire 602 back and forth, which in turn protrudes the electrode 400 from the distal end of the flexible catheter 228, or alternatively withdraws the spring electrode completely into the flexible catheter 228. Furthermore, the proximal end of the control wire 602 is connected to an RF electrical connector 604 mounted on the slider 600. An electrical cord (not shown) can be connected to this connector 604 to bring RF electrosurgical current from a standard electrosurgical generator (also not shown) to the device. The RF current then travels through the RF connector 604 and the control wire 602 to the electrode 400 connected to the leading end of the control wire 602.

While the present invention may be embodied with a handle having no stops or adjustments, the handle 606 of this embodiment has a stopper 700 fixed to the control wire 602 and stop nuts 702 and 704 which limit the movement range of the stopper 700 which moves together with the control wire 602.

Figure 14:
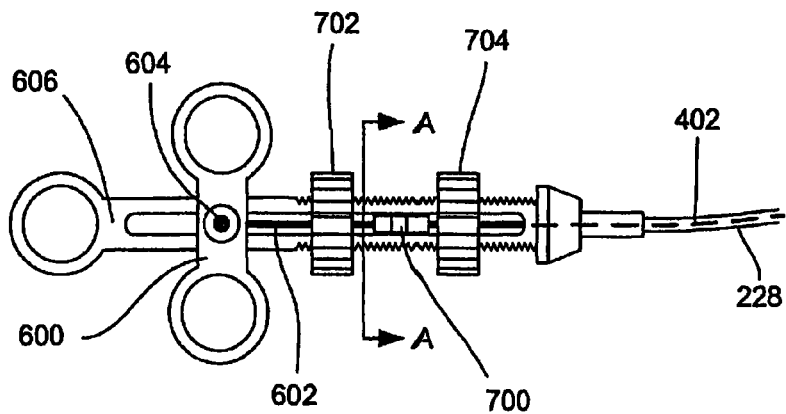
FIG. 14 is a plan view illustrating the constitution of a handle portion of the treatment device for endoscope of an embodiment of the present invention.
Figure 15:
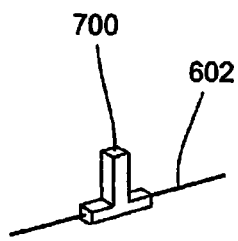
FIG. 15 is a perspective view illustrating a stopper of a control wire mounted on the handle portion of the treatment device for endoscope of the present invention.

FIG. 7 through FIG. 16 show a further detailed construction of the handle 606 of the embodiment shown in FIG. 13. A slider 600 on the handle 606 is attached to the proximal end of the control wire 602 which runs through the lumen of the flexible catheter 228. Movement of the slider 600 protrudes or retracts the preformed spring electrode 400 (not shown) on the distal end of the flexible catheter 228. A stopper 700 is affixed to the control wire 602 as illustrated in FIG. 14. This stopper 700 limits movement of the control wire 602. A proximally-positioned stop nut 702 limits movement of the control wire 602 as the slider 600 on the handle 606 is "closed," thereby limiting the degree that the electrode can be withdrawn into the distal end of the flexible catheter 228. A distally-positioned stop nut 704 conversely limits the degree that the handle can be "opened," thereby limiting the length of the electrode that protrudes from the distal end of the flexible catheter 228. As a result, the size of the hook shape formed by the spring electrode is limited.

Figure 16:
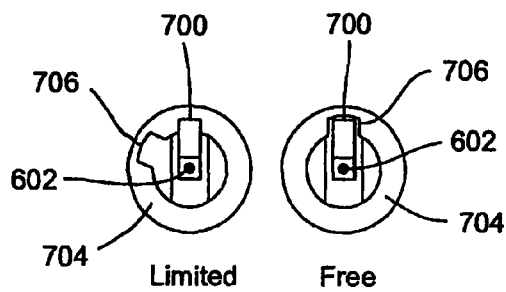
FIG. 16 is a sectional view of the handle portion taken along the line of A to A in FIG. 15, showing a state in which a stop nut for regulating the movable range of a stopper of the control wire is used to regulate the movement of the stopper and that in which it is used to release the regulation of the stopper.

In the embodiment illustrated in FIG. 14, the position of these maximum and minimum settings can be changed by the operator by changing the position of the threaded stop nuts 702 and 704 on the handle 606. Furthermore, each stop nut 702 and 704 has a cutout 706 which allows the stopper 700 to bypass the stop nut 702 and 704 when the stop nut is rotated into the free position, as illustrated in FIG. 16. This feature allows the operator to quickly put the handle 606 into a configuration in which the maximum and minimum limits of the control wire 602 movement are overridden. When the stop nuts 702 and 704 are put in the free configuration, the slider 600 can move back and forth freely without the stopper 700 encountering the stop nuts 702 and 704.

Figure 17:
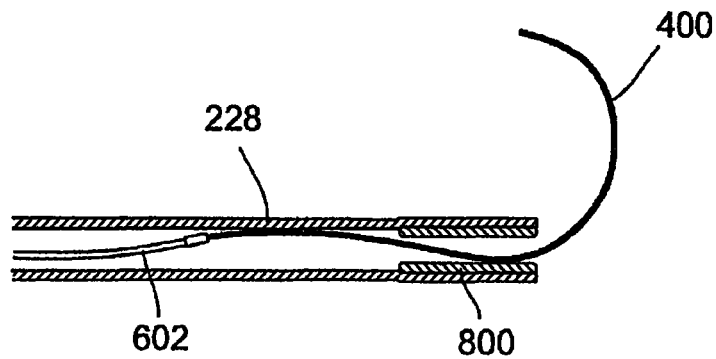
FIG. 17 shows a state in which a preformed spring electrode mounted on the treatment device for endoscope of the present invention is projected from the distal end of the catheter and fully extended.

FIG. 14 illustrates another embodiment of the treatment device for endoscope of the present invention. FIG. 17 illustrates that the preformed spring electrode 400 is constructed of a material such as Nitinol or a suitable spring metal such that when it is unconstrained it curls into a hook shape. This hook shape is essential for the electrode 400's ability to get behind body tissue and to incise them as the electrode is pulled towards the distal end of the endoscope. The material of the spring electrode 400 must also conduct RF current, in addition to having the ability to return to a predetermined shape. The spring electrode 400 is attached to the distal end of the control wire 602 which controls its movement in and out of the flexible catheter 228. In this embodiment the flexible catheter 228 is constructed of polymer tubing such as polytetrafluoroethylene (e.g., Teflon), but other materials are equally suitable. To constrain the distal end of the spring electrode 400 and to prevent it from scratching and catching on the inner wall of the polymer flexible catheter 228, a thin-walled metal sheath 800 is inserted into the distal end of the catheter 228.

Figure 18:
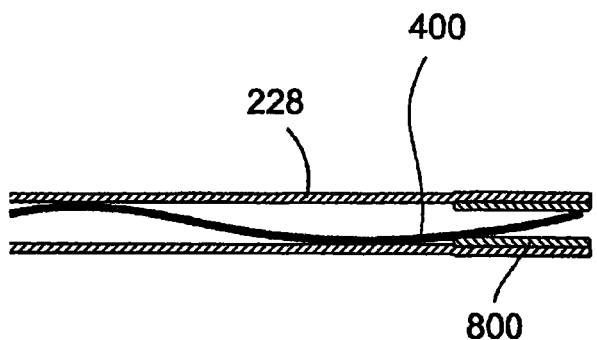
FIG. 18 shows a state in which the preformed spring electrode mounted on the treatment device for endoscope of the present invention is fully retracted into the catheter.

As FIG. 18 illustrates, when the preformed spring electrode 400 is completely retracted into the flexible catheter 228, it is totally constrained and lies within the lumen of the flexible catheter 228. In this configuration the device can be safely advanced into or retracted from the channel (inner lumen) of a flexible endoscope.

Figure 19:
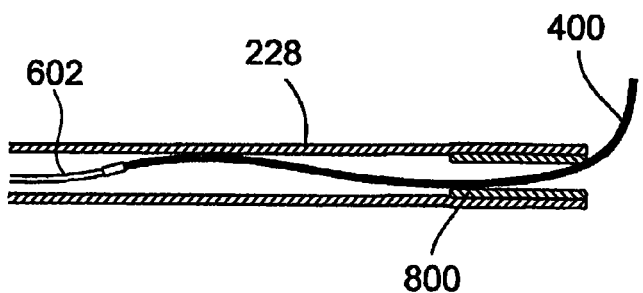
FIG. 19 shows a state in which the preformed spring electrode of the treatment device for endoscope of the present invention is partially projected from the catheter and other portions of the spring electrode are retracted into the catheter.

As FIG. 19 illustrates, it is possible to use the device in an intermediate position wherein the preformed spring electrode 400 protrudes only partially out of the distal end of the flexible catheter 228. In fact, the stop nuts 702 and 704 on the handle 606 illustrated in FIG. 4 are used to adjust the relative length of the spring electrode 400 which protrudes from the flexible catheter 228 as the handle 606 is operated between its maximum and minimum settings.

Figure 20:
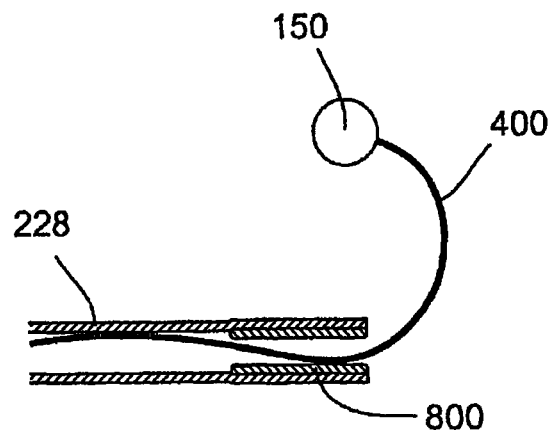
FIG. 20 is a view illustrating a modification of the preformed spring electrode mounted on the treatment device for endoscope of the present invention, in which an insulator is mounted at the leading end of the cutting electrode.

FIG. 20 illustrates an alternative embodiment of the preformed spring electrode 400. In this embodiment the distal end of the spring electrode 400 is covered by insulating material such as a ceramic bead, a polymer bead, or other material which cannot conduct RF current. As FIG. 21 illustrates, according to the embodiment, if the body tissue 500 being cut by the preformed spring electrode 400 is close to the other body tissue, the insulator chip 150 of the electrode 400 prevents these adjacent body tissues 502 from contacting the energized metal portion of the cutting electrode 400.

Figure 21:
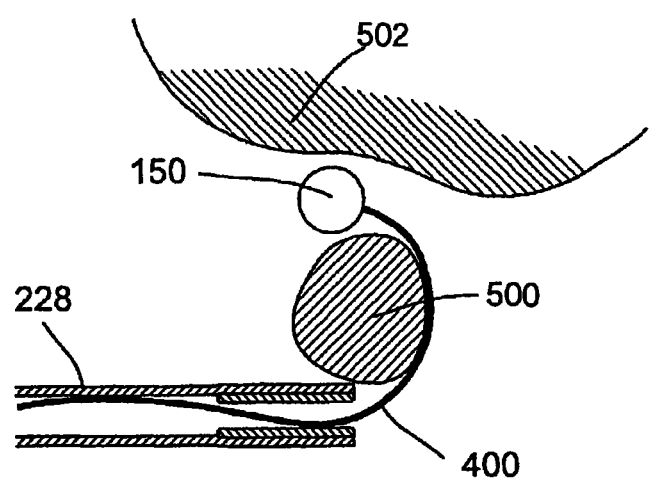
FIG. 21 is a view showing a state in which the treatment device for endoscope shown in FIG. 11 is used to hook the body tissue to be cut by the preformed spring electrode.
Figure 22:
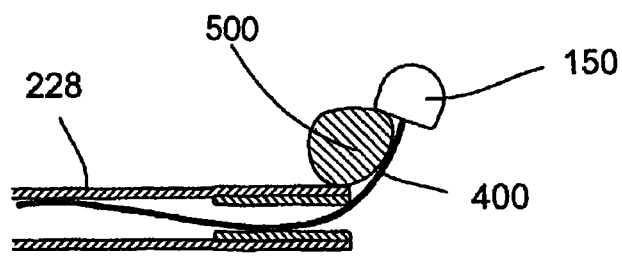
FIG. 22 is a view illustrating another modification of the preformed spring electrode of the treatment device for endoscope of the present invention, in which changed is a configuration of the insulator mounted at the leading end of the cutting electrode.

FIG. 22 shows a modification of the embodiment shown in FIG. 21, illustrating that the size and shape of the insulator chip 150 of the device may have a shape designed specifically to help capture and hold the body tissue which the device is intended to cut.

Although FIG. 7 and FIG. 9 illustrate that the method and apparatus of the present invention has application in endoscopic transgastric surgery (by way of example—the procedure of female sterilization), the present invention has many other broad applications. It can be used in rigid endoscopic (e.g., laparoscopic) surgery as well as all forms of flexible endoscopic surgery. The device is well suited for incising large structures such as the fallopian tubes herein illustrated. However, the device can also be made proportionally smaller with a smaller hook and/or catheter. Smaller embodiments of the present invention will be useful for incising exposed blood vessels, ducts, nerves, connective body tissue, muscle fibers, omentum, etc.

Next, a description will be given for other embodiments of the present invention.

Figure 23:
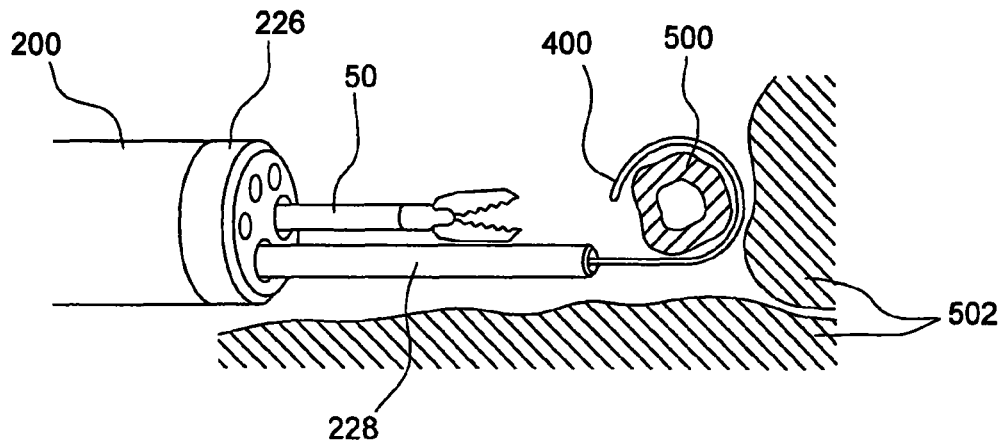
FIG. 23 is a view illustrating a modification of the treatment device for endoscope of the present invention, showing a state in which the body tissue to be cut is hooked by the preformed spring electrode.
Figure 24:
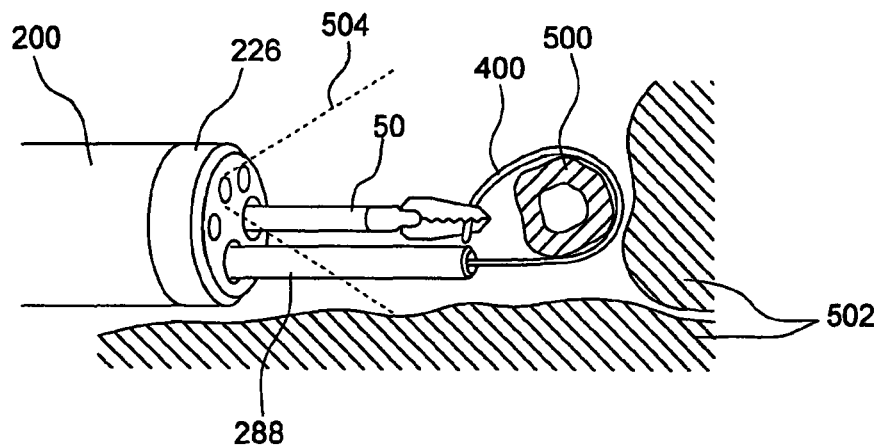
FIG. 24 shows a state in which the leading end of the preformed spring electrode hooking the body tissue to be cut is grasped by using grasping forceps passed through a channel different from that of the electrode in the treatment device for endoscope shown in FIG. 23.

The treatment device for endoscope of the present invention shown in FIG. 23 and FIG. 24 is constituted with the treatment device for endoscope shown in FIG. 13 and a grasping forceps 50 as a restraint instrument. In the treatment device for endoscope, at first, as illustrated in FIG. 23, the distal end 226 of the insertion tube 200 of the endoscope is disposed between the body tissue 500 to be cut and other adjacent body tissues to be preserved 502, and a flexible catheter 228 is projected through the channel of an insertion tube 200 from the distal end 226 thereof. Then, as illustrated in FIG. 24, when a handle 606 of the treatment device is operated to project a preformed spring electrode 400 from the distal end of the flexible catheter 228, the electrode 400 recovers a bent configuration which has been imparted in advance, thereby the electrode 400 is hooked onto the body tissue 500 to be cut. Then, the grasping forceps 50 is projected through another channel of the insertion tube 200 from the distal end 226, and the leading end of the electrode 400 is grasped by the grasping forceps 50. Then, the flexible catheter 228 including the electrode 400 and the grasping forceps 50 is pulled into the channel of the insertion tube 200 in synchronization and the body tissue 500 to be cut is pulled and drawn away from the adjacent body tissues 502. Then, the electrode 400 hooking the body tissue 500 is moved to the distal end 226 of the insertion tube 200, and RF current is applied to the electrode 400, thereby the body tissue 500 is incised. After incision of the body tissue 500, the grasping forceps 50 is operated to release the leading end of the electrode 400, thereby forcibly pulling the electrode 400 into the catheter 228. Then, the electrode 400 is retracted into the catheter 228, while being linearly extended to resemble the configuration of the catheter 228.

As described above, the grasping forceps 50 is used to grasp the leading end of electrode 400, thereby preventing the electrode 400 from undergoing an unintended deformation due to a reaction force acting on the electrode 400 from the body tissue 500 to be cut. Then, the electrode 400 is joined to the grasping forceps 50 to secure the body tissue 500 to be cut thereinside, thereby the electrode 400 can incise the body tissue 500 to be cut without fail. Further, all operations can be performed while the treatment is observed from start to finish under a visual field 504 of the endoscope.

Figure 25:
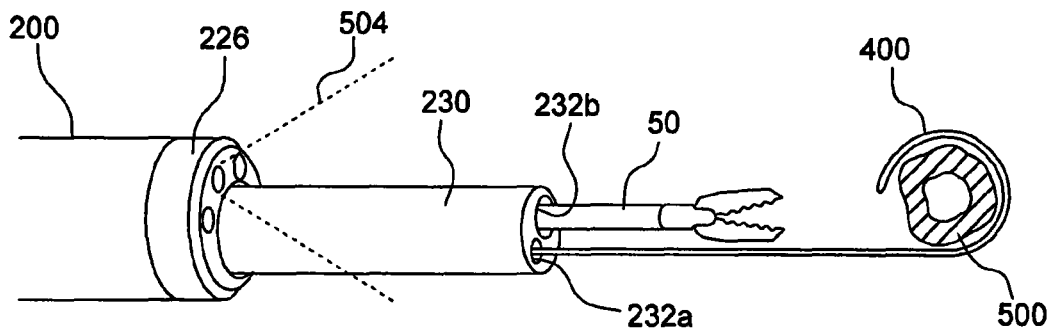
FIG. 25 is a view illustrating a modification of the treatment device for endoscope of the present invention, showing a state in which the body tissue to be cut is hooked by the preformed spring electrode.
Figure 26:
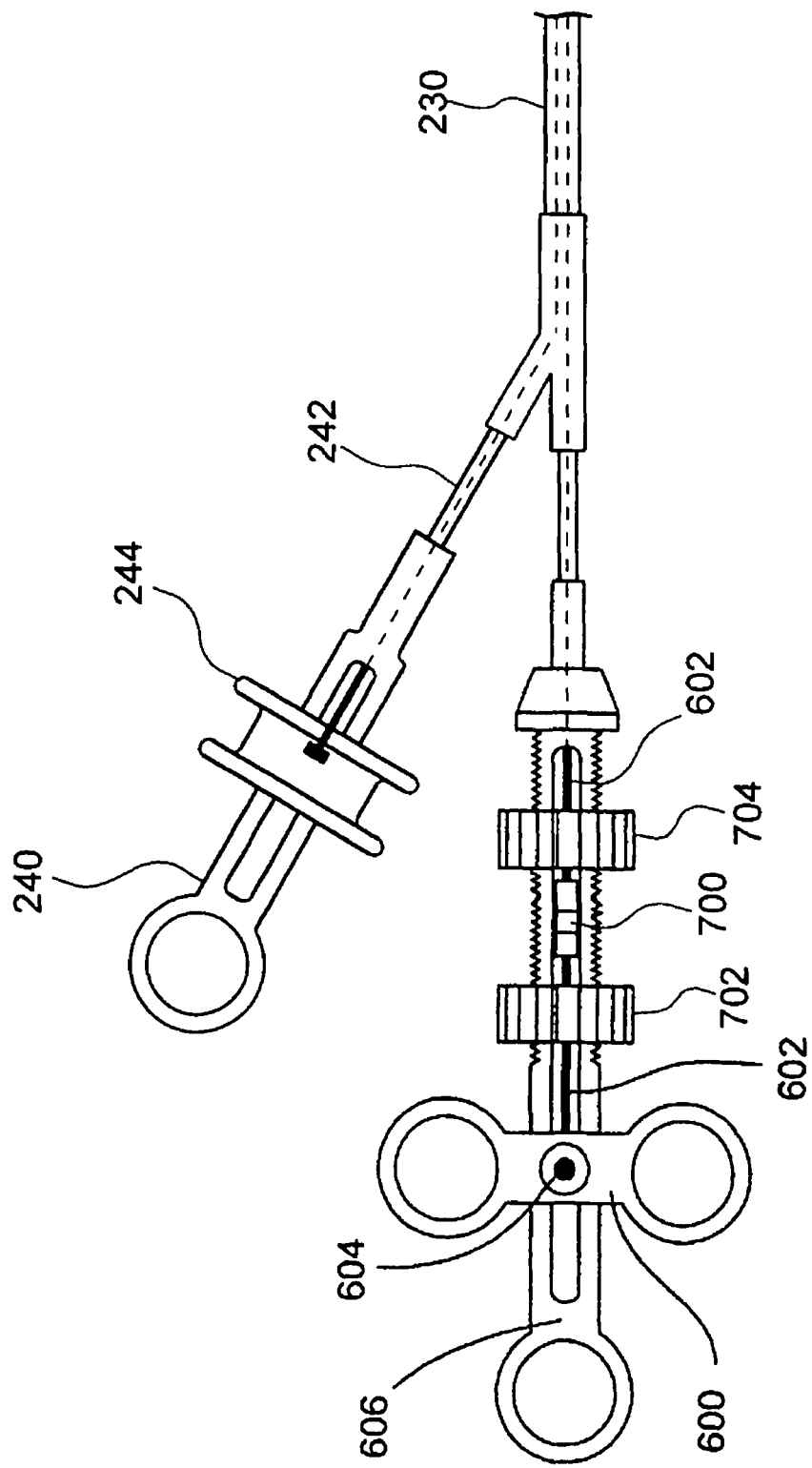
FIG. 26 is a view illustrating a modification of the treatment device for endoscope of the present invention, or a plan view illustrating a treatment device provided with a handle for operating the preformed spring electrode and a handle for operating the grasping forceps.

The treatment device for endoscope of the present invention shown in FIG. 25 and FIG. 26 is constituted with a flexible catheter 230, a control wire 602 passed through the flexible catheter 230, a preformed spring electrode 400 connected to the distal end of a control wire 602, a handle 606 mounted on the proximal end of the flexible catheter 230, the grasping forceps 50 passed through the flexible catheter 230, and a handle 240 of the grasping forceps 50 mounted on the proximal end of the flexible catheter 230.

As illustrated in FIG. 25, the flexible catheter 230 is provided with a lumen 232a through which a control wire 602 of the electrode 400 is passed and another lumen 232b through which the grasping forceps 50 is passed. As illustrated in FIG. 26, the proximal end of the flexible catheter 230 is branched into two directions. A handle 606 for operating the electrode 400 is mounted at one proximal end, and a handle 240 for operating the grasping forceps 50 is mounted at the other proximal end. The handle 240 is provided with a slider 244 for pushing and pulling a control wire 242 to open or close a pawl at the leading end of the grasping forceps 50. When the slider 244 of the handle 240 is moved back and forth, the control wire 24 is moved back and forth, thereby the claw at the leading end of the grasping forceps 50 is opened or closed.

In the thus constituted treatment device for endoscope, at first, the distal end 226 of the insertion tube 200 of the endoscope is disposed between the body tissue 500 to be cut and other adjacent body tissues, and a flexible catheter 230 is projected through the channel of the insertion tube 200 from the distal end 226. Then, as illustrated in FIG. 25, when a handle 606 of the treatment device is operated to project an electrode 400 from the distal end of the flexible catheter 230, the electrode 400 recovers a bent configuration which has been imparted in advance, thereby the electrode 400 is hooked onto the body tissue 500 to be cut. Then, a handle 240 is operated to project the grasping forceps 50 from the distal end 226 of the flexible catheter 230, and the leading end of the electrode 400 is grasped by the grasping forceps 50. Then, the flexible catheter 230 including the electrode 400 and the grasping forceps 50 are pulled into the channel of the insertion tube 200 and the body tissue 500 to be cut is pulled and drawn away from adjacent body tissues. Then, the electrode 400 hooking the body tissue 500 is moved to the distal end 226 of the insertion tube 200, and RF current is applied to the electrode 400, thereby the body tissue 500 is incised. After incision of the body tissue 500, the grasping forceps 50 is operated to release the leading end of the electrode 400, thereby forcibly pulling the electrode 400 into the catheter 230. As a result, the electrode 400 is retracted into the catheter 230 while being linearly extended to resemble the configuration of the catheter 230.

As described above, the grasping forceps 50 is used to grasp the leading end of the electrode 400, thereby making it possible to incise the body tissue 500 to be cut by using the electrode 400 without fail. Further, all operations can be performed while the treatment is observed from start to finish under the visual field 504 of the endoscope.

Figure 27:
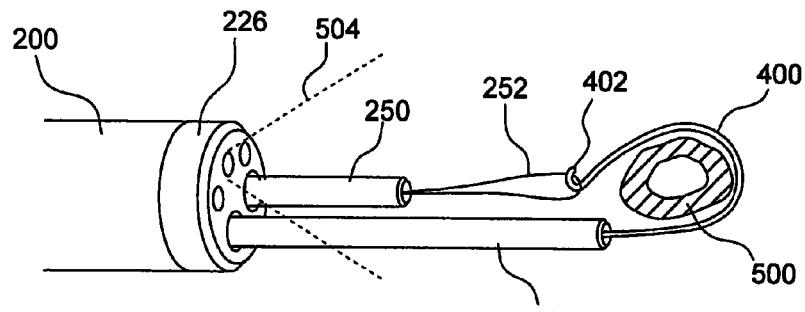
FIG. 27 is a view illustrating a modification of the treatment device for endoscope of the present invention, showing a state in which the leading end of the preformed spring electrode hooking the body tissue to be cut is restrained by using a loop of a snare passed through a channel different from that of the electrode.

The treatment device for endoscope of the present invention shown in FIG. 27 is provided with a snare 250 as a restraint instrument in place of the grasping forceps 50. Further, the leading end of the preformed spring electrode 400 is provided with a hook portion 402 for hooking the loop 252 of the snare 250.

In this treatment device for endoscope, at first, the distal end 226 of the insertion tube 200 of the endoscope is disposed between the body tissue 500 to be cut and other adjacent body tissues, and a flexible catheter 228 is projected through the channel of the insertion tube 200 from the distal end 226. Then, when a handle 606 of the treatment device is operated to project an electrode 400 from the distal end of the flexible catheter 228, the electrode 400 recovers a bent configuration which has been imparted in advance, thereby the electrode 400 is hooked onto the body tissue 500 to be cut. Then, the snare 250 is projected through another channel of the insertion tube 200 from the distal end 226 and the snare 250 is operated to hook the loop 252 onto the hook portion 402 of the electrode 400. Then, the flexible catheter 228 including the electrode 400 and the snare 250 are pulled into the channel of the insertion tube 200 in synchronization, and the body tissue 500 to be cut is pulled and drawn away from the adjacent body tissues. Then, the electrode 400 hooking the body tissue 500 is moved to the distal end 226 of the insertion tube 200, and RF current is applied to the electrode 400, thereby the body tissue 500 is incised. After incision of the body tissue 500, the snare 250 is operated to release the leading end of the electrode 400, thereby forcibly pulling the electrode 400 into the catheter 228. As a result, the electrode 400 is retracted into the catheter 228 while being linearly extended to resemble the configuration of the catheter 228.

As described above, the snare 250 is used to grasp the leading end of the electrode 400, thereby making it possible to incise the body tissue 500 to be cut by using the electrode 400 without fail. Further, all operations can be performed while the treatment is observed from start to finish under a visual field 504 of the endoscope.

Figure 28:
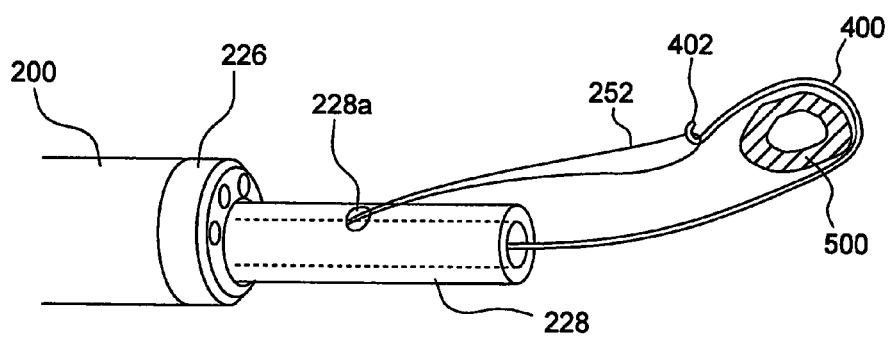
FIG. 28 is a view illustrating a modification of the treatment device for endoscope of the present invention, showing a state in which the leading end of the preformed spring electrode hooking the body tissue to be cut is restrained by using a loop of a snare projected from a through hole formed on the side wall of the catheter.

Moreover, in the present embodiment, treatment is performed by using the endoscope having two channels of an insertion tube 200. However, as illustrated in FIG. 28, it is possible to perform treatment by using an endoscope having only one channel of an insertion tube 200. In this instance, a through hole 228a is formed on the side wall at the distal end of the catheter 228, and a loop 252 which constitutes a snare is passed through the through hole 228a.

In this treatment device for endoscope, at first, the distal end 226 of the insertion tube 200 of the endoscope is disposed between the body tissue 500 to be cut and other adjacent body tissues, and a flexible catheter 228 is projected through the channel of the insertion tube 200 from the distal end 226. Then, when a handle 606 of the treatment device is operated to project a preformed spring electrode 400 from the distal end of the flexible catheter 228, the electrode 400 recovers a bent configuration which has been imparted in advance, thereby the electrode 400 is hooked onto the body tissue 500 to be cut. Then, a loop 252 is operated and hooked onto a hook portion 402 of the electrode 400. Then, the flexible catheter 228 including the electrode 400 and the loop 252 is pulled into the channel of the insertion tube 200, and the body tissue 500 to be cut is pulled and drawn away from the adjacent body tissues. Then, the electrode 400 hooking the body tissue 500 is moved to the distal end 226 of the insertion tube 200, and RF current is applied to the electrode 400, thereby the body tissue 500 is incised. As described above, the loop 252 constituting a snare is passed through a through hole 228a formed on the side wall at the distal end of the catheter 228, thereby the loop 252 separates from the distal end of the catheter 228. Therefore, the loop 252 can easily catch the hook portion 402 at the leading end of the electrode 400.

Figure 29:
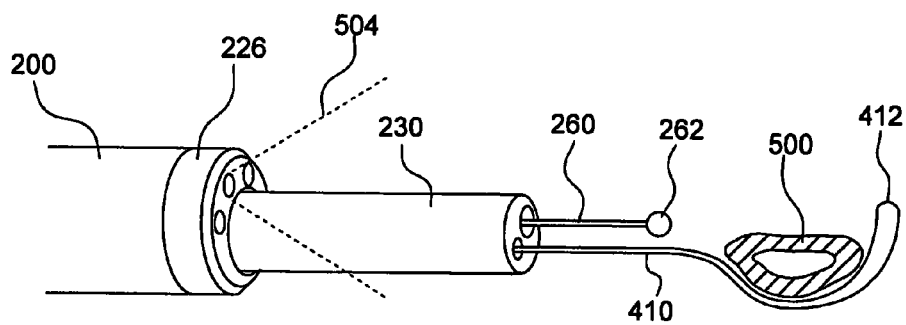
FIG. 29 is a view illustrating a modification of the treatment device for endoscope of the present invention, showing a state in which the body tissue to be cut is hooked by the preformed spring electrode.
Figure 30:
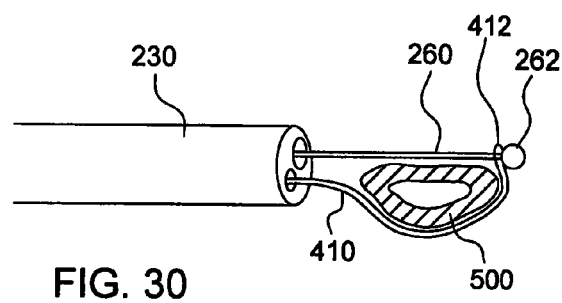
FIG. 30 shows a state in which the leading end of the preformed spring electrode hooking the body tissue to be cut is restrained by using a traction instrument passed through a channel the same as that of the electrode in the treatment device for endoscope shown in FIG. 29.

The treatment device for endoscope of the present invention shown in FIG. 29 and FIG. 30 is provided with a preformed spring electrode 410 as a cutting electrode and a traction instrument 260 as a restraint instrument. The leading end of the traction instrument 260 is projected from the distal end of a flexible catheter 230. A loop 412 is provided at the leading end of the preformed spring electrode 410. Further, a ball portion 262 for hooking the loop 412 of the electrode 410 is provided at the leading end of the traction instrument 260.

A control wire 602 of the electrode 400 is passed through a lumen 232a of the flexible catheter 230, and the traction instrument 260 is passed through another lumen 232b. Although not illustrated, the proximal end of the flexible catheter 230 is branched into two directions. A handle for operating the electrode 410 is mounted at one proximal end, and a handle for operating the traction instrument 260 is mounted at the other proximal end. When the handle for the traction instrument 260 is operated, the ball portion 262 mounted at the leading end of the traction instrument 260 is moved back and forth.

In this treatment device for endoscope, at first, the distal end 226 of the insertion tube 200 of the endoscope is disposed between the body tissue 500 to be cut and other adjacent body tissues, and a flexible catheter 230 is projected through the channel of the insertion tube 200 from the distal end 226. Then, as illustrated in FIG. 29, when a handle of the treatment device is operated to project an electrode 410 from the distal end of the flexible catheter 230, the electrode 410 recovers a bent configuration which has been imparted in advance, thereby the electrode 410 is hooked onto the body tissue 500 to be cut. Then, as illustrated in FIG. 30, a traction instrument 260 is operated to hook a ball portion 262 onto a loop 412 of the electrode 410. Then, the flexible catheter 230 including the electrode 410 and the traction instrument 260 is pulled into the channel of the insertion tube 200; and the body tissue 500 to be cut is pulled and drawn away from the adjacent body tissues. Then, the electrode 410 hooking the body tissue 500 is moved to the distal end 226 of the insertion tube 200, and RF current is applied to the electrode 410, thereby the body tissue 500 is incised. After incision of the body tissue 500, the traction instrument 260 is operated to release the loop 412 of the electrode 410, thereby forcibly pulling the electrode 410 into the catheter 230. As a result, the electrode 410 is retracted into the catheter 230 while being linearly extended to resemble the configuration of the catheter 230.

As described above, the traction instrument 260 is used to grasp the leading end of the electrode 410, thereby it is possible to incise the body tissue 500 to be cut by using the electrode 410 without fail. Further, all operations can be performed while the treatment is observed from start to finish under a visual field 504 of the endoscope.

Figure 31:
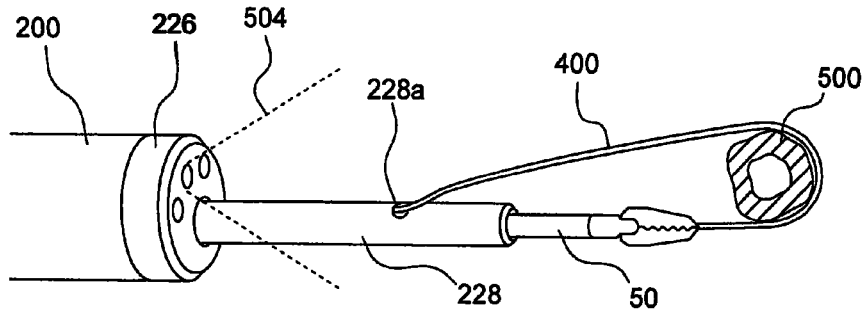
FIG. 31 is a view illustrating a modification of the treatment device for endoscope of the present invention, showing a state in which the leading end of the preformed spring electrode projected from the through hole formed on the side wall of the catheter and having hooked the body tissue to be cut is restrained by using the grasping forceps projected from the distal end of the catheter.

In the treatment device for endoscope of the present invention shown in FIG. 31, the preformed spring electrode 400 as a cutting electrode is projected from a through hole 228a formed on the side wall at the distal end of the catheter 228, and the grasping forceps 50 is projected from an opening at the distal end of the catheter 228. Although not illustrated, the proximal end of the flexible catheter 228 is branched into two directions. A handle for operating the electrode 400 is mounted at one proximal end of the flexible catheter 228, and a handle for operating the grasping forceps 50 is mounted at the other proximal end of the flexible catheter 228.

In the thus constituted treatment device for endoscope, at first, the distal end 226 of the insertion tube 200 of the endoscope is disposed between the body tissue 500 to be cut and other adjacent body tissues, and the flexible catheter 228 is projected through the channel of the insertion tube 200 from the distal end 226. Then, when a handle of the treatment device is operated to project the electrode 400 from a through hole 228a of the flexible catheter 230, the electrode 400 recovers a bent configuration which has been imparted in advance, thereby the electrode 400 is hooked onto the body tissue 500 to be cut. Then, a handle is operated to project grasping forceps 50 from the distal end of the flexible catheter 228, and the leading end of the electrode 400 is grasped by the grasping forceps 50. Then, the flexible catheter 228 including the electrode 400 and the grasping forceps 50 are pulled into the channel of the insertion tube 200 and the body tissue 500 to be cut is pulled and drawn away from adjacent body tissues. Then, the electrode 400 hooking the body tissue 500 is moved to the distal end 226 of the insertion tube 200, and RF current is applied to the electrode 400, thereby the body tissue 500 is incised. After incision of the body tissue 500, the grasping forceps 50 is operated to release the leading end of the electrode 400, thereby forcibly pulling the electrode 400 into the catheter 228. As a result, the electrode 400 is retracted into the catheter 228 while being linearly extended to resemble the configuration of the catheter 228.

As described above, the grasping forceps 50 is used to grasp the leading end of the electrode 400, thereby it is possible to incise the body tissue 500 to be cut by using the electrode 400 without fail. Further, all operations can be performed while the treatment is observed from start to finish under a visual field 504 of the endoscope. Further, the grasping forceps 50 is passed through the through hole 228a formed on the side wall at the distal end of the catheter 228, thereby the grasping forceps 50 separates from the distal end of the catheter 228. Therefore, the grasping forceps 50 can easily catch the leading end of the electrode 400.

Figure 32:
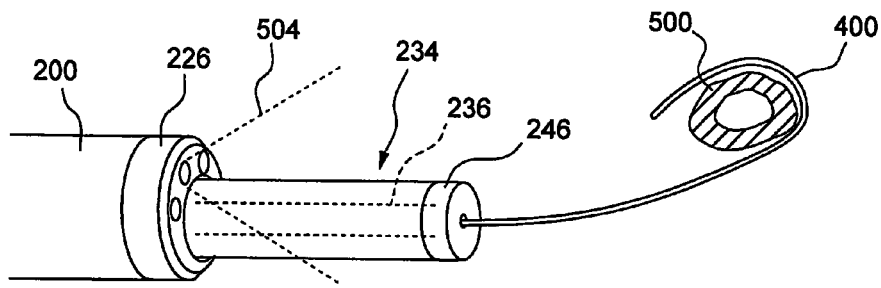
FIG. 32 is a view illustrating a modification of the treatment device for endoscope of the present invention, showing a state in which the body tissue to be cut is hooked by the preformed spring electrode projected from the distal end of a double-structured catheter.
Figure 33:
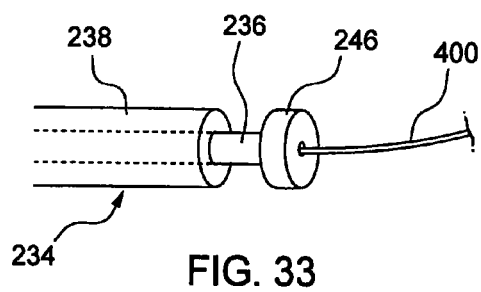
FIG. 33 shows a grasping structure of the preformed spring electrode mounted on the side wall of the catheter in the treatment device for endoscope shown in FIG. 32.
Figure 34:
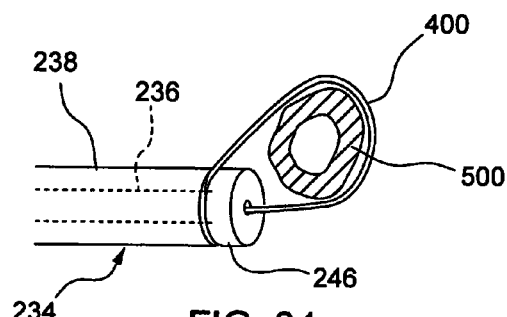
FIG. 34 shows a state in which the leading end of the preformed spring electrode hooking the body tissue to be cut is grasped by using the grasping structure formed on the side wall of the catheter in the treatment device for endoscope shown in FIG. 32.

In the treatment device for endoscope of the present invention shown in FIG. 32 through FIG. 34, the catheter 234 acts as a restraint instrument. As illustrated in FIG. 32, the catheter 234 is provided with a double structure made up of an inner sheath 236 and an outer sheath 238, and a control wire 602 of the electrode 400 is passed through the inner sheath 236. The inner sheath 236 is slidable back and forth with respect to the outer sheath 238. A disk 246 which is approximately as large as the outer diameter of the outer sheath 238 is fixed at the distal end of the inner sheath 236 in such a way that an opening at the distal end of the inner sheath 236 is exposed at the center. When the inner sheath 236 is allowed to slide with respect to the outer sheath 238 so as to be pulled backward, the disk 246 is brought into contact with the distal end face of the outer sheath 238. Although not illustrated, the proximal end of the flexible catheter 234 is branched into two directions. A handle for operating the electrode 400 is mounted at one proximal end of the flexible catheter 234, and a handle for operating the inner sheath 236 is mounted at the other proximal end of the flexible catheter 234.

In the thus constituted treatment device for endoscope, at first, the distal end 226 of the insertion tube 200 of the endoscope is disposed between the body tissue 500 to be cut and other adjacent body tissues, and the flexible catheter 234 is projected through the channel of the insertion tube 200 from the distal end 226. Then, as illustrated in FIG. 32, when a handle of the treatment device is operated to project an electrode 400 from the distal end of the catheter 234, the electrode 400 recovers a bent configuration which has been imparted in advance, thereby the electrode 400 is hooked onto the body tissue 500 to be cut. Then, as illustrated in FIG. 33, the handle is operated to move the inner sheath 236 forward with respect to the outer sheath 238, thereby the disk 246 separates from the distal end face of the outer sheath 238. Then, as illustrated in FIG. 34, the electrode 400 is inserted into a space between the disk 246 and the distal end face of the outer sheath 238, and the inner sheath 236 is this time moved backward with respect to the outer sheath 238, thereby interposing the leading end of the electrode 400 between the disk 246 and the distal end face of the outer sheath 238. Then, the flexible catheter 234 including the electrode 400 is pulled into the channel of the insertion tube 200, and the body tissue 500 to be cut is pulled and drawn away from adjacent body tissues. Then, the electrode 400 hooking the body tissue 500 is moved to the distal end 226 of the insertion tube 200, and RF current is applied to the electrode 400, thereby the body tissue 500 is incised. After incision of the body tissue 500, the catheter 234 is operated to release the leading end of the electrode 400, thereby forcibly pulling the electrode 400 into the catheter 234. As a result, the electrode 400 is retracted into the catheter 234 while being linearly extended to resemble the configuration of the catheter 234.

As described above, the catheter 234 is used to grasp the leading end of the electrode 400, thereby it is possible to incise the body tissue 500 to be cut by using the electrode 400 without fail. Further, all operations can be performed while the treatment is observed from start to finish under the visual field 504 of the endoscope.

Figure 35:
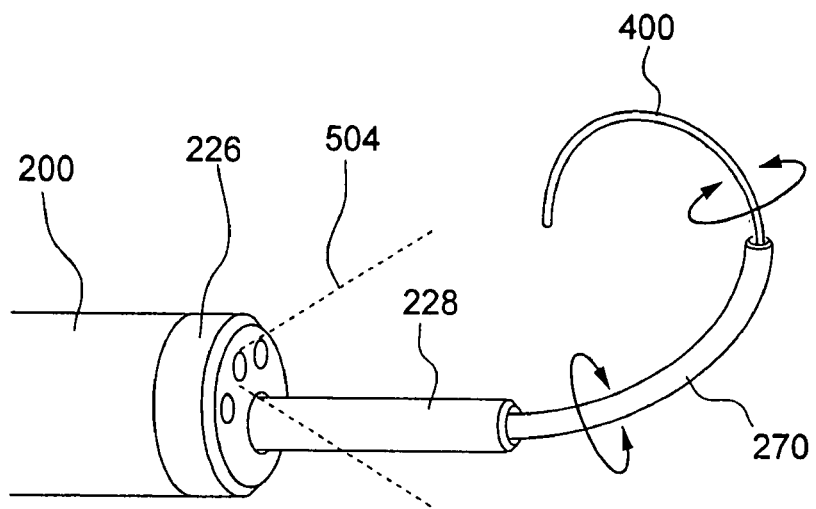
FIG. 35 is a view illustrating a modification of the treatment device for endoscope of the present invention, showing a treatment device capable of changing the configuration of the preformed spring electrode in a three-dimensional manner.
Figure 36:
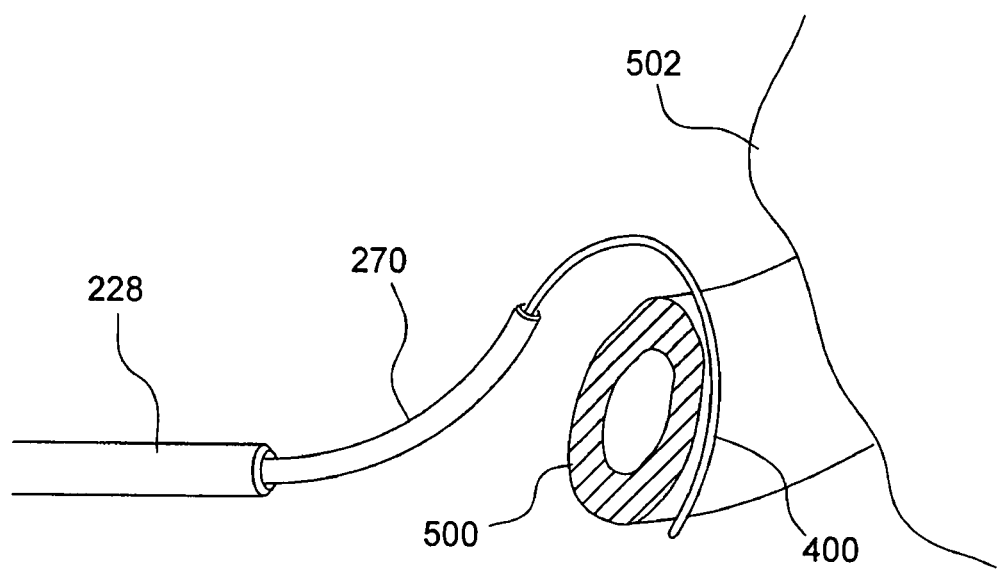
FIG. 36 shows a state in which the preformed spring electrode is changed in configuration to hook the body tissue to be cut in the treatment device for endoscope shown in FIG. 35.

In the treatment device for endoscope of the present invention shown in FIG. 35 and FIG. 36, the preformed spring electrode 400 can freely obtain a three-dimensional configuration. As illustrated in FIG. 32, a control wire 602 of the electrode 400 is passed through a flexible sheath 270, and the flexible sheath 270 through which the control line 602 is passed is inserted into the catheter 228. The flexible sheath 270 can be freely rotated with respect to the catheter 228 in a circumferential direction. The control wire 602 can also be freely rotated with respect to the flexible sheath 270 in a circumferential direction. The flexible sheath 270 is made of an insulating material and imparted at the distal end thereof in advance with a bent configuration so as to give an arc. The electrode 400 is also imparted at the leading end thereof in advance with a bent configuration so as to give an arc. The control wire 602 of the electrode 400 is rotated with respect to the flexible sheath 270 in a circumferential direction, thereby a three-dimensional bent configuration to the electrode 400 is imparted.

In the thus constituted treatment device for endoscope, at first, the distal end 226 of the insertion tube 200 of the endoscope is disposed between the body tissue 500 to be cut and other adjacent body tissues, and the catheter 228 is projected through the channel of the insertion tube 200 from the distal end 226. Then, as illustrated in FIG. 35, when the control wire 602 is pressed into the flexible sheath 270, with the flexible sheath 270 restrained with respect to the catheter 228, and the electrode 400 is projected from the distal end of the catheter 228, the electrode 400 recovers a bent configuration which has been imparted in advance. Further, when the flexible sheath 270 is pressed into the catheter 228, with the control wire 602 restrained with respect to the flexible sheath 270, and the flexible sheath 270 is projected from the distal end of the catheter 228, the flexible sheath 270 also recovers a bent configuration which has been imparted in advance. Then, as illustrated in FIG. 36, the control wire 602 is rotated with respect to the flexible sheath 270 in a circumferential direction, thereby the electrode 400 is displaced so as to turn toward the distal end of the flexible sheath 270. Each of the distal end of the flexible sheath 270 and the electrode 400 is provided with an arc-like bent configurations in advance. Therefore, when the electrode 400 is displaced as described above, the leading end of the treatment device including the electrode 400 and the distal end of the flexible sheath 270 obtain a three-dimensional bent configuration. Further, the three-dimensional configuration changes according to an extent to which the electrode 400 is displaced with respect to the distal end of the flexible sheath 27. As described above, the electrode 400 is freely changed in configuration according to the configuration and dimension of the body tissue 500 to be cut, thereby it is possible to accurately secure only the body tissue 500 in separation from other adjacent body tissues. After incision of the body tissue 500, the electrode 400 and the flexible sheath 270 are forcibly pulled into the catheter 228. As a result, the electrode 400 and the flexible sheath 270 are retracted into the catheter 228 while being linearly extended to resemble the configuration of the catheter 228.

Figure 37:
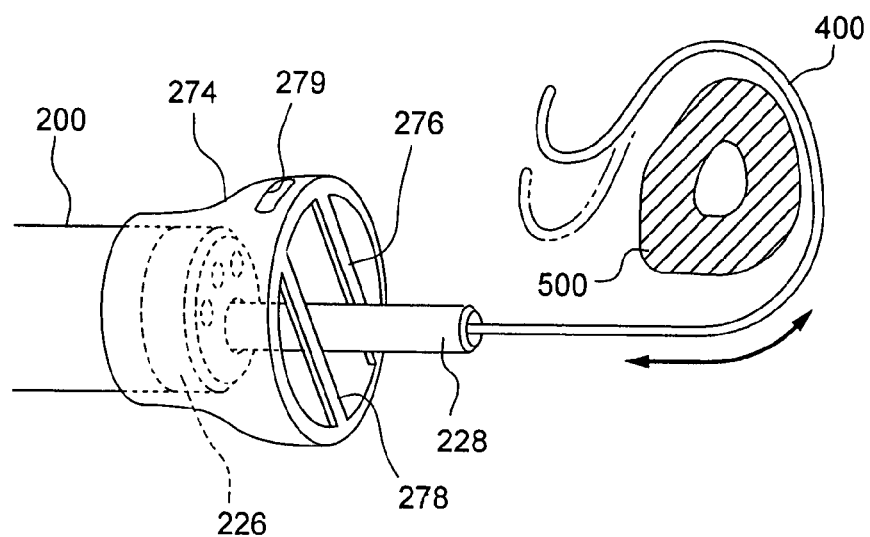
FIG. 37 is a view illustrating a modification of the treatment device for endoscope of the present invention, showing a treatment device which has at the distal end of the catheter a cap capable of holding the body tissue to be cut between the cap and the preformed spring electrode.
Figure 38:
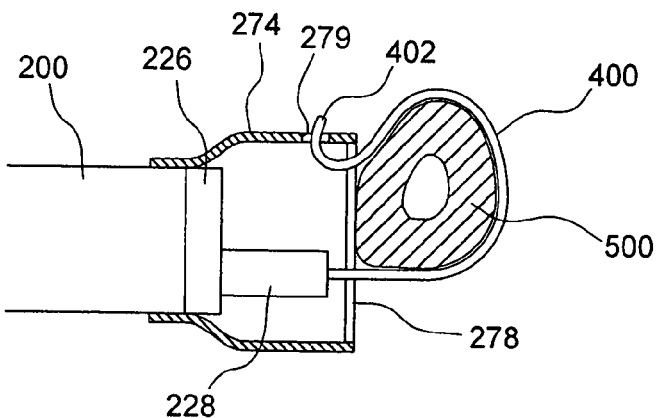
FIG. 38 shows a state in which the body tissue to be cut is held between the cap and the preformed spring electrode in the treatment device for endoscope shown in FIG. 37.

The treatment device for endoscope of the present invention shown in FIG. 37 and FIG. 38 is provided with a cap 274 wrapped at the distal end of the catheter 228. The cap 274 is provided with a contact face 276 for holding the body tissue 500 to be cut between itself and a preformed spring electrode 400. The contact face 276 is formed at the distal end of the cap 274 wrapped at the distal end of the catheter 228, that is, at a site further away from the distal end of the catheter 228, so as to be approximately parallel with the distal end face of the catheter 228. The contact face 276 is provided with three slits in such a way that the visual field of the endoscope is not restricted or the radiation of illumination light is not prevented in a state that the cap 274 is wrapped at the distal end of the catheter 228. The electrode 400 is projected from a slit 278 at the center, which is the largest among these three slits. Further, the cap 274 is provided with a hook hole (cutting-electrode fixing portion) 279 for hooking a hook portion 402 mounted at the leading end of the electrode 400.

In the thus constituted treatment device for endoscope, at first, the distal end 226 of the insertion tube 200 of the endoscope is disposed between the body tissue 500 to be cut and other adjacent body tissues, and the flexible catheter 228 is projected through the channel of the insertion tube 200 from the distal end 226. Then, when a handle of the treatment device is operated to project the electrode 400 from the distal end of the flexible catheter 228, as illustrated in FIG. 37, the electrode 400 recovers a bent configuration that has been imparted in advance. Therefore, the electrode 400 is hooked onto the body tissue 500 to be cut and the electrode 400 is further projected from the distal end of the flexible catheter 228, thereby the electrode 400 is bent to a greater extent, thereby the hook portion 402 of the electrode 400 is close to the catheter 228. Then, the catheter 228 including the electrode 400 is pulled into the channel of the insertion tube 200, and the body tissue 500 to be cut is pulled and drawn away from adjacent body tissues. Then, the catheter 228 is further pulled into the channel of the insertion tube 200, thereby the body tissue 500 is held between the contact face 276 of the cap 274 and the electrode 400. As illustrated in FIG. 38, the hook portion 403 of the electrode 400 is inserted into the slit 276. Then, when the control wire 602 is pulled into the catheter 228, the electrode 400 deforms so as to be bent to a lesser extent, and the hook portion 402 is hooked onto a hook hole 279 from inside of the cap 274. Thereby, the leading end of the electrode 400 is fixed to the cap 274. Therefore, the electrode 400 forms a loop to secure the body tissue 500 to be cut thereinside, it is possible to incise the body tissue 500 to be cut by using the electrode 400 without fail. After incision of the body tissue 500, the electrode 400 is forcibly pulled into the catheter 228, thereby the hook portion 402 is removed from the hook hole 279, and the electrode 400 can be retracted into the catheter 228.

Figure 39:
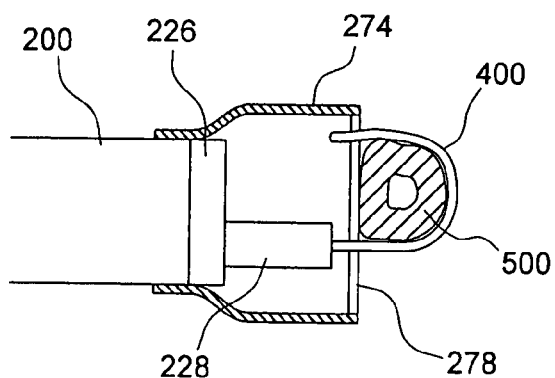
FIG. 39 is a modification of the treatment device for endoscope shown in FIG. 37, showing a treatment device from which a hook portion at the leading end of the electrode is deleted due to an increased rigidity of the preformed spring electrode.

Moreover, in the present embodiment, the hook portion 402 is provided at the leading end of the electrode 400. However, if the electrode 400 is high in rigidity, there is no need for providing the hook portion 402 or providing the hook hole 279 at the cap 274. When the catheter 228 including the electrode 400 is pulled into the channel of the insertion tube 200, the body tissue 500 is held between the contact face 276 of the cap 274 and the electrode 400, and the leading end of the electrode 400 is inserted into the slit 278. Then, when a control wire 602 is pulled into the catheter 228, as illustrated in FIG. 39, the electrode 400 deforms so as to be bent to a lesser extent and the leading end thereof is hooked onto the edge of the slit 278. Thereby, the leading end of the electrode 400 is fixed to the cap 274.

Figure 40:
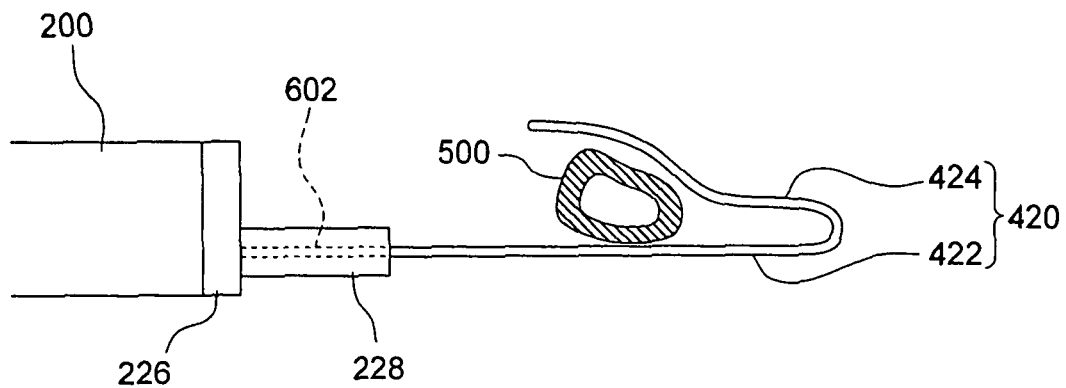
FIG. 40 is a view illustrating a modification of the treatment device for endoscope of the present invention, showing a treatment device provided with the preformed spring electrode bent approximately in a V-letter shape.
Figure 41:
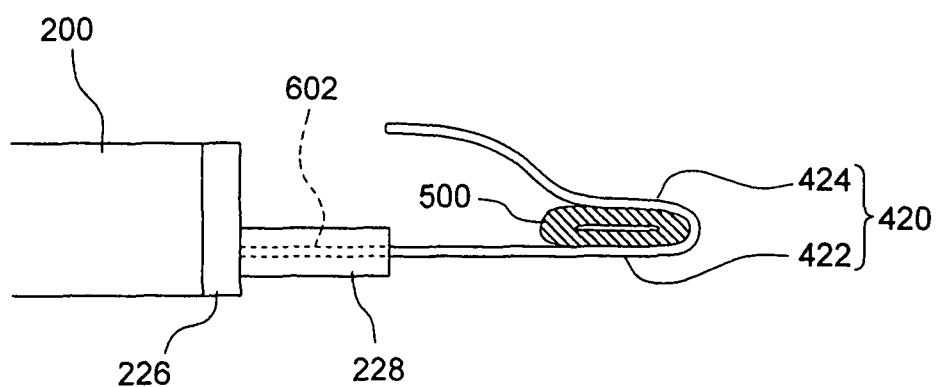
FIG. 41 shows a state in which the body tissue to be cut is held by the preformed spring electrode of the treatment device for endoscope shown in FIG. 40.

The treatment device for endoscope of the present invention shown in FIG. 40 and FIG. 41 is provided with a preformed spring electrode 420 which is bent approximately in a V-letter shape in advance. The electrode 420 is composed of a proximal portion 422 forming one side of the V-letter shape and continuing to the control wire 602, and a distal portion 424 forming the other side of the V-letter shape and continuing to the proximal portion 422. The distal portion 424 is bent in such a way as to be folded back with respect to the proximal portion 422. A space between the proximal portion 422 and the distal portion 424 is made narrower as it moves away from the distal end of the control wire 602. The distal portion 424 is not linear in configuration but bent so as to be rapidly brought closer to the proximal portion 422 as it moving away from the distal end of the control wire 602. The electrode 420 is inserted into the catheter 228, in a state that it is folded so that the distal portion 424 is firmly attached to the proximal portion 422.

In the thus constituted treatment device for endoscope, at first, the distal end 226 of the insertion tube 200 of the endoscope is disposed between the body tissue 500 to be cut and other adjacent body tissues, and the flexible catheter 228 is projected through the channel of the insertion tube 200 from the distal end 226. Then, when a handle of the treatment device is operated to project the electrode 420 from the distal end of the flexible catheter 228, as illustrated in FIG. 40, the electrode 420 recovers a bent configuration that has been imparted in advance, and the electrode 420 is then hooked onto the body tissue 500 to be cut. Then, when the catheter 228 including electrode 420 is pulled into the channel of the insertion tube 200, as illustrated in FIG. 41, the body tissue 500 is entered into a rapidly narrowed space between the proximal portion 422 and the distal portion 424, and held by an elastic force acting between the proximal portion 422 and the distal portion 424. Thereby, the body tissue 500 is compressed to result in an increased hemostatic effect. Further, since the electrode 420 is strongly pressed to the body tissue 500, an electric current is supplied to the body tissue 500 at a greater density, thereby cutting performance of the electrode 420 is improved. After incision of the body tissue 500, the electrode 420 is forcibly pulled into the catheter 228. As a result, the electrode 420 is retracted into the catheter 228 while being linearly extended to resemble the configuration of the catheter 228.

Figure 42:
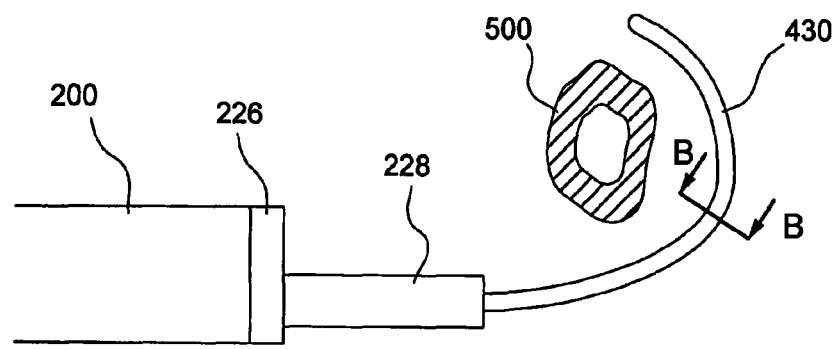
FIG. 42 is a view illustrating a modification of the treatment device for endoscope of the present invention, showing a treatment device having the preformed spring electrode, the cross section of which is an oval.
Figure 43:
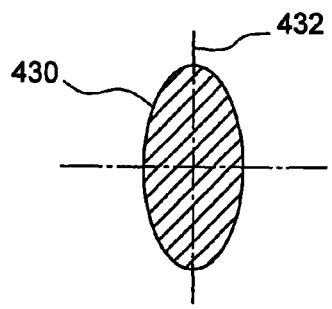
FIG. 43 is a sectional view illustrating the preformed spring electrode taken along the line B to B in FIG. 42.

The treatment device for endoscope of the present invention shown in FIG. 42 and FIG. 43 is provided with a preformed spring electrode 430 having an oval cross section. As illustrated in FIG. 43, the cross section of the electrode 430 is an oval in which the length of the arc of the electrode 430 in the direction of a first axis 432 from inside to outside is longer than the length in the direction of a second axis 434 orthogonal to the first axis 432. In other words, the cross section of the electrode 430 is an oval having the first axis 432 as a long axis and the second axis 434 as a short axis.

In the thus constituted treatment device for endoscope, when the body tissue 500 to be cut is hooked by the electrode 430, the electrode 430 intends to be difficult to deform so as to eliminate the bent configuration. Therefore, even if the catheter 228 including the electrode 430 is pulled strongly, the electrode 430 is less likely to be removed from the body tissue 500. Thereby, the electrode 430 can incise the body tissue 500 without fail.

Incidentally, in the present embodiment, the electrode 430 has an oval shaped in cross section. However, the cross section is not restricted to an oval shape but may be a rectangular shape, as long as the above conditions are met.

Figure 44:
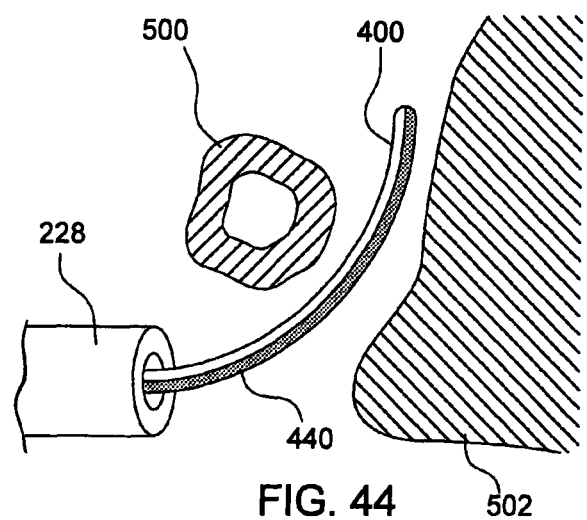
FIG. 44 is a view illustrating a modification of the treatment device for endoscope of the present invention, showing a treatment device in which the preformed spring electrode is partially covered by an insulator.

In the treatment device for endoscope of the present invention shown in FIG. 44, an insulator 440 is provided along the preformed spring electrode 400. The insulator 440 covers the inside of the arc of the electrode 400, that is, a portion excluding that which is pressed to the body tissue 500 to be cut. Thereby, adjacent body tissues 502 around the body tissue 500 to be cut are not damaged to result in an increase in safety.

Figure 45:
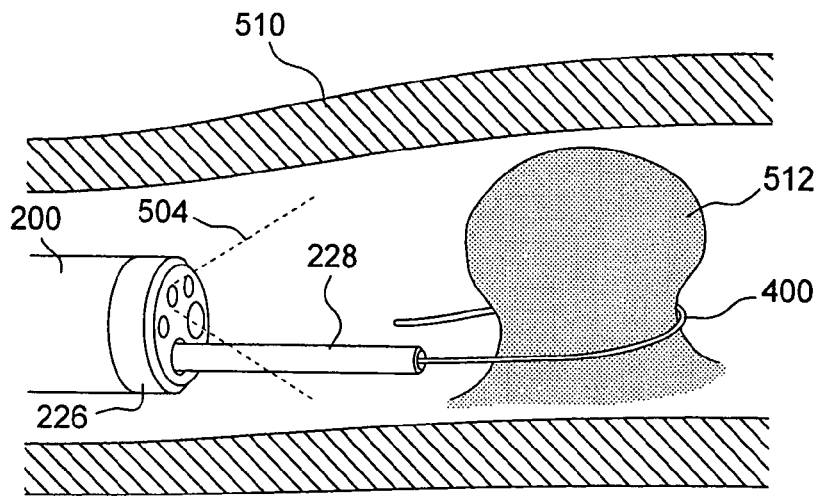
FIG. 45 is a view explaining a technique for removing a polyp growth on the large intestine by using the treatment device for endoscope shown in FIG. 23, showing a state in which an insertion tube of the endoscope is inserted into the large intestine and the polyp is hooked by using the preformed spring electrode which has been hooked.
Figure 46:
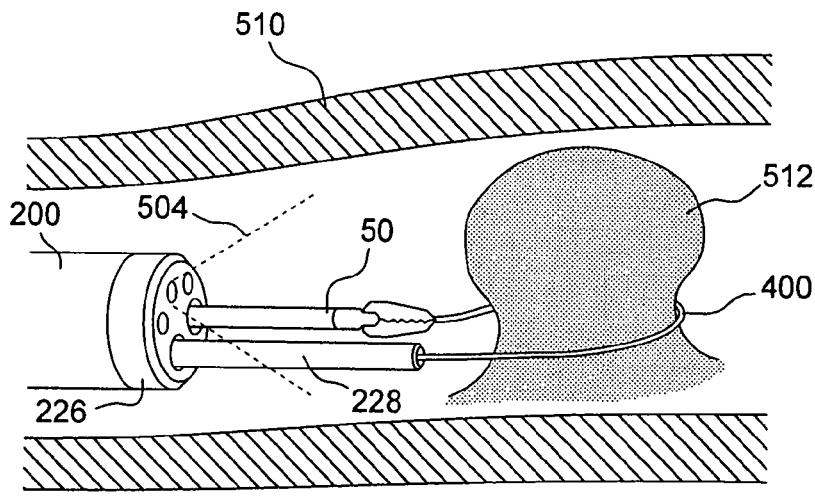
FIG. 46 shows a state in which the insertion tube of the endoscope is inserted into the large intestine and the leading end of the preformed spring electrode hooking the polyp is grasped by the grasping forceps.
Figure 47:
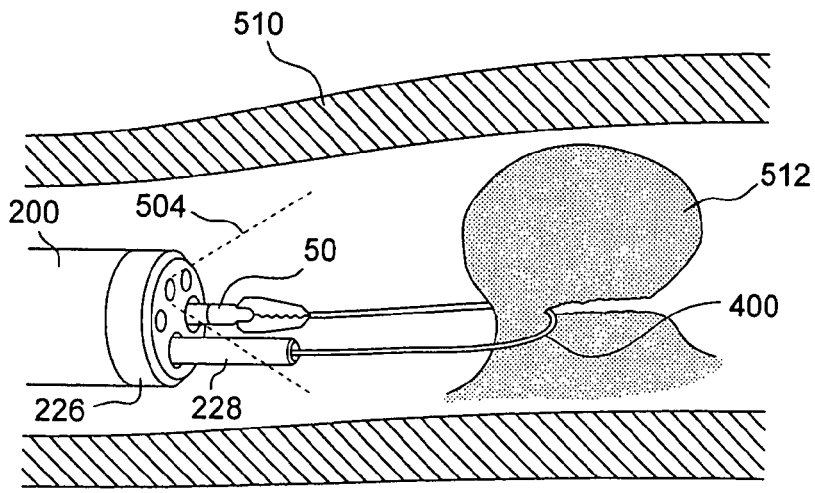
FIG. 47 shows a state in which an electric current is supplied to the electrode to remove the polyp, while traction is applied to the polyp by using the preformed spring electrode and the grasping forceps.

Next, a description will be made with reference to FIG. 45 through FIG. 47 for a technique removing a polyp growth on the large intestine by using the treatment device for endoscope shown in FIG. 23.

First, an insertion tube 200 of the endoscope is inserted into the large intestine 510. Then, the distal end 226 of the insertion tube 200 of the endoscope is disposed in front of a polyp to be cut 512, and a flexible catheter 228 is projected through the channel of the insertion tube 200 from the distal end 226. Then, as illustrated in FIG. 45, when a handle 606 of the treatment device is operated to project a preformed spring electrode 400 from the distal end of the flexible catheter 228, the electrode 400 recovers a bent configuration that has been imparted in advance, thereby the electrode 400 is hooked onto the root of the polyp 512. Then, as illustrated in FIG. 46, grasping forceps 50 is projected through another channel of the insertion tube 200 from the distal end 226, thereby the grasping forceps 50 can grasp the leading end of the electrode 400. Then, the flexible catheter 228 including the electrode 400 and the grasping forceps 50 are pulled into the channel of the insertion tube 200 in synchronization, and the polyp 512 is pulled. While the electrode 400 hooking the polyp 512 is moved toward the distal end 226 of the insertion tube 200, RP current is applied to the electrode 400, thereby incising the root of the polyp 512. After incision of the polyp 512, the electrode 400 is forcibly pulled into the catheter 228. Then, the electrode 400 is retracted into the catheter 228, while being linearly extended to resemble the configuration of the catheter 228.

The above-described treatment makes it possible to remove the polyp 512 by using the electrode 400 without fail. Further, all operations can be performed while the treatment is observed from start to finish under the visual field 504 of the endoscope.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A treatment device for endoscope used for cutting body tissue, the treatment device being capable of projecting to and retracting from a catheter of the endoscope, the treatment device comprising:
    a control wire inserted into the catheter;
    a restraint instrument provided in the catheter so as to be capable of being projected from the catheter; and
    a cutting electrode in which a proximal end portion thereof is connected with a distal end of the control wire; wherein
    the restraint instrument is configured to move freely on an axial line which is approximately parallel to the control wire;
    the cutting electrode has a bent configuration when unrestrained such that a leading end of the cutting electrode curves towards a proximal end direction when projected from the catheter, and the cutting electrode is capable of deforming elastically so as to fit within the catheter when the cutting electrode is retracted inside the catheter, the cutting electrode being configured to be capable of recovering the bent configuration when projecting the leading end of the cutting electrode from the catheter so that the leading end of the cutting electrode is provided to intersect the axial line; and
    the restraint instrument and the leading end of the cutting electrode are arranged such that the restraint instrument is capable of restraining the leading end of the cutting electrode along the axial line.

2. The treatment device for endoscope according to claim 1, wherein the restraint instrument is a grasping forceps for grasping the leading end of the cutting electrode.

3. The treatment device for endoscope according to claim 1, wherein
    a loop is provided at one of the leading end of the restraint instrument and the leading end of the cutting electrode, and
    a hook portion of hooking the loop is provided at the other of the leading end of the restraint instrument and the leading end of the cutting electrode.

4. The treatment device for endoscope according to claim 1, wherein
    the restraint instrument is projected from an opening at the distal end of the catheter, and
    the cutting electrode is projected from a through hole formed on the side wall at the distal end of the catheter.

5. The treatment device for endoscope according to claim 1, wherein the bent configuration of the cutting electrode comprises a three-dimensional bent configuration.

6. The treatment device for endoscope according to claim 5, further comprising:
    a flexible sheath into which the control wire is inserted, the flexible sheath and the control wire being inserted into the catheter; wherein
    the distal end of the flexible sheath is imparted in advance with a bent configuration, and
    the control wire is rotated with respect to the flexible sheath in a circumferential direction, thereby imparting the cutting electrode with the three-dimensional bent configuration.

7. The treatment device for endoscope according to claim 1, wherein
    the cutting electrode is bent approximately in a V-letter shape,
    the cutting electrode has a proximal portion continuing to the control wire and a distal portion continuing to the proximal portion, the distal portion being folded back with respect to the proximal portion, and
    a space between the proximal portion and the distal portion is made narrower as it moves away from the distal end of the control wire.

8. The treatment device for endoscope according to claim 1, wherein the cutting electrode has a cross section in which the length of the arc of the cutting electrode in the direction of a first axis from inside to outside is longer than the length in the direction of a second axis orthogonal to the first axis.

9. The treatment device for endoscope according to claim 1, wherein the cutting electrode is covered with an insulator at a portion excluding a portion which is pressed to the body tissue to be cut.

10. The treatment device for endoscope according to claim 1, further comprising:
    a projected-length adjusting portion for adjusting a projected length from the distal end of the catheter in the cutting electrode.

11. The treatment device for endoscope according to claim 10, wherein the projected-length adjusting portion is provided with a stopper for regulating a maximum projected length of the cutting electrode.

12. The treatment device for endoscope according to claim 1, wherein
the catheter is made of an insulating material,
a metal sheath is fitted inside the distal end of the catheter, and
the leading end of the cutting electrode is disposed inside the metal sheath in a state where the cutting electrode is retracted into the catheter.

13. The treatment device for endoscope according to claim 1, wherein an insulator is provided at the leading end of the cutting electrode.

14. The treatment device for an endoscope according to claim 1, wherein the catheter has a first lumen into which the control wire is inserted and a second lumen into which the restraint instrument is inserted.

* * * * *